(12) United States Patent
He et al.

(10) Patent No.: US 12,035,974 B2
(45) Date of Patent: Jul. 16, 2024

(54) METHOD FOR DETERMINING TARGET SPOT PATH

(71) Applicant: HANGZHOU SANTAN MEDICAL TECHNOLOGY CO., LTD, Zhejiang (CN)

(72) Inventors: Bin He, Zhejiang (CN); Liping Shen, Zhejiang (CN); Shuogui Xu, Zhejiang (CN); Shigui Yan, Zhejiang (CN); Weixu Li, Zhejiang (CN); Sisheng Li, Zhejiang (CN); Hanqing Chen, Zhejiang (CN); Rui Tong, Zhejiang (CN); Qi Xu, Zhejiang (CN); Hualei Fang, Zhejiang (CN); Weiwei Sun, Zhejiang (CN); Hongrui Guo, Zhejiang (CN)

(73) Assignee: HANGZHOU SANTAN MEDICAL TECHNOLOGY CO., LTD, Hangzhou (CN)

( * ) Notice: Subject to any disclaimer, the term of this patent is extended or adjusted under 35 U.S.C. 154(b) by 401 days.

(21) Appl. No.: 17/431,683

(22) PCT Filed: Mar. 4, 2020

(86) PCT No.: PCT/CN2020/077846
§ 371 (c)(1),
(2) Date: Aug. 17, 2021

(87) PCT Pub. No.: WO2020/177725
PCT Pub. Date: Sep. 10, 2020

(65) Prior Publication Data
US 2022/0133409 A1    May 5, 2022

(30) Foreign Application Priority Data

Mar. 4, 2019  (CN) .......................... 201910161263.3
Mar. 4, 2019  (CN) .......................... 201910161265.2
(Continued)

(51) Int. Cl.
*A61B 34/10*    (2016.01)
*A61B 34/20*    (2016.01)
(Continued)

(52) U.S. Cl.
CPC .............. *A61B 34/10* (2016.02); *A61B 34/20* (2016.02); *G06T 7/80* (2017.01); *G06V 10/26* (2022.01);
(Continued)

(58) Field of Classification Search
CPC ... A61B 34/10; A61B 34/20; A61B 2034/107; A61B 2034/2065; A61B 90/13;
(Continued)

(56) References Cited

U.S. PATENT DOCUMENTS 11,553,969 B1 *   1/2023  Lang ..................... G06T 7/0012
11,779,192 B2 * 10/2023  Rossetto ................ A61B 34/30
                                                                 600/103
(Continued)

FOREIGN PATENT DOCUMENTS

CN        106420052 A    2/2017
CN        106794044 A    5/2017
(Continued)

OTHER PUBLICATIONS

International Search Report of PCT/CN2020/077846.
Written Opinion of PCT/CN2020/077846.

*Primary Examiner* — Santiago Garcia

(57) ABSTRACT

The present disclosure relates to a method for determining a target spot path, which is applied to a determining system
(Continued)

including a shooting device and a locating device that are separate from each other, and a calibration device connected to the shooting device, the method comprising: S1. obtaining a three-dimensional partial image for an affected part and a virtual path located in the three-dimensional partial image; S2. matching a simulated two-dimensional image obtained based on projection of the three-dimensional partial image with a two-dimensional projection image obtained based on the affected part; S3. determining a surgical guide path on the two-dimensional projection image that corresponds to the virtual path according to position information of the virtual path on the simulated two-dimensional image, when the simulated two-dimensional image and the two-dimensional projection image are matched; and/or S4.

17 Claims, 11 Drawing Sheets

(30) Foreign Application Priority Data

| Mar. 4, 2019 | (CN) | 201910161266.7 |
| Mar. 4, 2019 | (CN) | 201910161268.6 |
| Mar. 4, 2019 | (CN) | 201910161726.6 |

(51) Int. Cl.
  *G06T 7/80* (2017.01)
  *G06V 10/26* (2022.01)
  *G06V 10/50* (2022.01)

(52) U.S. Cl.
  CPC ........ *G06V 10/50* (2022.01); *A61B 2034/107* (2016.02); *A61B 2034/2065* (2016.02)

(58) Field of Classification Search
  CPC .......... A61B 90/50; A61B 2017/00725; A61B 2090/363; A61B 2090/376; A61B 2560/0437; A61B 90/37; G06T 7/80; G06V 10/26; G06V 10/50; G06V 2201/03; G06V 10/24; G06V 10/761; G06V 20/647
  See application file for complete search history.

(56) References Cited

U.S. PATENT DOCUMENTS

| 2007/0135803 | A1* | 6/2007 | Belson | A61B 1/00154 |
| | | | | 606/1 |
| 2012/0106819 | A1* | 5/2012 | Fernandez Oca | A61B 34/10 |
| | | | | 382/132 |
| 2015/0150523 | A1* | 6/2015 | Sirpad | G06T 15/00 |
| | | | | 382/132 |
| 2017/0316561 | A1* | 11/2017 | Helm | A61B 34/20 |
| 2018/0099157 | A1* | 4/2018 | Prieels | A61B 5/743 |
| 2019/0125461 | A1* | 5/2019 | Zheng | G06N 3/08 |
| 2022/0079675 | A1* | 3/2022 | Lang | G02B 30/52 |

FOREIGN PATENT DOCUMENTS

| CN | 107679574 A | 2/2018 |
| CN | 109044529 A | 12/2018 |
| CN | 109195527 A | 1/2019 |
| CN | 109925052 A | 6/2019 |
| CN | 109925053 A | 6/2019 |
| CN | 109925054 A | 6/2019 |
| CN | 109993792 A | 7/2019 |

* cited by examiner

METHOD FOR DETERMINING TARGET SPOT PATH

CROSS-REFERENCE TO RELATED APPLICATIONS

This Application is a national stage application of PCT/CN2020/077846. The present application claims priorities from PCT Application No. PCT/CN2020/077846, filed Mar. 4, 2020, and from the following Chinese patent applications filed with the Chinese National Intellectual Property Administration on Mar. 4, 2019: CN201910161726.6, titled "Projection Method, Device and System and Readable Storage Medium"; CN201910161268.6, titled "Auxiliary Method, Device and System for Determining Target Spot Path, and Readable Storage Medium"; CN201910161263.3, titled "Method, Device and System for Determining Target Spot Path, and Readable Storage Medium"; CN201910161265.2, titled "Locating System and Target Spot Locating Method"; and CN201910161266.7, titled "Method, Device and System for Determining Surgical Path, and Readable Storage Medium", the entire contents of which are incorporated into the present application by reference.

FIELD OF THE INVENTION

The present application relates to the field of medical technology, and in particular to a method for determining a target spot path.

BACKGROUND

At present, when surgical instruments are used to perform an operation on an affected part, it is usually necessary to insert the surgical instruments into the interior of the affected part to accurately obtain a path inside an affected limb, which can greatly improve the accuracy of the operation, reduce the number of X-ray shootings, reduce radiation, and relieve the pain of the patient. Based on the importance of the path, how to improve the accuracy of the path has become a technical problem that needs to be solved urgently by people.

SUMMARY OF THE INVENTION

The present application provides a method for determining a target spot path to solve the deficiencies in the related art.

According to a first aspect of the embodiments of the present application, a method for determining a target spot path is provided, which is applied to a determining system including a shooting device and a locating device that are separate from each other, and a calibration device connected to the shooting device, in which the locating device includes a pointing structure, and the method for determining the target spot path includes:

S1. obtaining a three-dimensional partial image for an affected part and a virtual path located in the three-dimensional partial image;

S2. matching a simulated two-dimensional image obtained based on projection of the three-dimensional partial image with a two-dimensional projection image obtained based on the affected part;

S3. determining a surgical guide path based on the two-dimensional projection image that corresponds to the virtual path according to position information of the virtual path on the simulated two-dimensional image, when the simulated two-dimensional image and the two-dimensional projection image are matched; and/or S4. obtaining three-dimensional posture information of the virtual path on the three-dimensional partial image as perspective coordinate information of the surgical guide path based on a perspective coordinate system, when the simulated two-dimensional image and the two-dimensional projection image are matched, in which the perspective coordinate system is formed based on the shooting device; and adjusting the pointing structure according to the perspective coordinate information of the surgical guide path, and a second conversion relationship between the perspective coordinate system and a locating coordinate system based on the locating device, so that a pointing direction of the pointing structure is matched with the surgical guide path corresponding to the virtual path.

Optionally, in step S2, the step of matching the simulated two-dimensional image obtained based on the projection of the three-dimensional partial image with the two-dimensional projection image obtained based on the affected part includes:

S21. performing a perspective projection on the affected part to obtain the two-dimensional projection image;

S22. projecting the three-dimensional partial image to obtain the simulated two-dimensional image; and S23. obtaining a degree of coincidence of the simulated two-dimensional image and the two-dimensional projection image, and determining that the simulated two-dimensional image is matched with the two-dimensional projection image when the degree of coincidence is not smaller than a preset threshold.

Optionally, in step S23, the step of obtaining the degree of coincidence of the simulated two-dimensional image and the two-dimensional projection image includes:

extracting a first projection area in the simulated two-dimensional image and a second projection area in the two-dimensional projection image; and calculating the degree of coincidence according to a degree of edge contour matching between the first projection area and the second projection area.

Optionally, in step S23, the step of obtaining the degree of coincidence of the simulated two-dimensional image and the two-dimensional projection image includes:

segmenting both the simulated two-dimensional image and the two-dimensional projection image in a preset direction according to a preset ratio; and matching each segmented area of the simulated two-dimensional image with a corresponding segmented area of the two-dimensional projection image to obtain the degree of coincidence.

Optionally, in step S23, if the degree of coincidence is smaller than the preset threshold, a spatial posture of the three-dimensional partial image is adjusted; and/or projection parameters for the three-dimensional partial image are adjusted.

Optionally, the step of adjusting the spatial posture of the three-dimensional partial image includes at least one of the following:

adjusting a rotational angle of the three-dimensional partial image with respect to at least one coordinate axis; and adjusting a displacement of the three-dimensional partial image with respect to at least one coordinate axis; and the step of adjusting the projection parameters for the three-dimensional partial image includes at least one of the following:

adjusting a focal length;
adjusting a position of a virtual light source; and
adjusting an imaging resolution, in which the imaging resolution is related to a size of a projection imaging plane of the three-dimensional partial image and an image size of the simulated two-dimensional image.

Optionally, in step S3, the method further includes:

S31. obtaining first image position information of a plurality of position points on the two-dimensional projection image that correspond to the virtual path; and S32. adjusting the pointing structure based on the first image position information, so that the pointing direction of the pointing structure sequentially points to a plurality of target spots at the affected part that correspond to a plurality of position points on the surgical guide path.

Optionally, in step S32, the step of adjusting the pointing structure based on the first image position information includes:

obtaining image position information of a projection path on the two-dimensional projection image that is matched with the virtual path, according to image position information of the virtual path on the simulated two-dimensional image; and adjusting the pointing structure according to image position information of a plurality of position points on the projection path.

Optionally, the calibration device includes a calibration plate and a first identification plate, the calibration plate is provided with a plurality of first preset mark points, and the first identification plate is provided with a plurality of second preset mark points; in a projection direction, the calibration plate and the first identification plate are arranged in parallel with each other at an interval;

in step S32, the step of adjusting the pointing structure based on the first image position information includes:

obtaining calibration position information of each of the first preset mark points on a first plane and each of the second preset mark points on a second plane in a calibration coordinate system;

obtaining image position information of each of the first preset mark points on the first plane and each of the second preset mark points on the second plane in an image coordinate system, the image coordinate system being formed based on a projection image of the calibration device; and adjusting the pointing structure according to the calibration position information and the image position information of the first preset mark points, the calibration position information and the image position information of the second preset mark points, and the first image position information of any position point on the virtual path.

Optionally, the method further includes:

determining a first conversion relationship between the calibration coordinate system and the image coordinate system according to the calibration position information of the plurality of first preset mark points on the calibration device in the calibration coordinate system and the image coordinate information of the plurality of first preset mark points on the calibration device in the image coordinate system; and obtaining the calibrated two-dimensional projection image according to the first conversion relationship.

Optionally, the locating device includes a second identification plate which is provided with a plurality of third preset mark points, and the calibration device is separate from the locating device; and the second conversion relationship is obtained in the following manner:

obtaining the first conversion relationship between the calibration coordinate system and the image coordinate system and focal point position information of the shooting device; and determining the second conversion relationship according to the focal point position information of the shooting device, locating coordinate information of the second identification plate in the locating coordinate system, the first conversion relationship and image coordinate information of the second identification plate in the image coordinate system, in which the perspective coordinate system is related to the focal point position information.

Optionally, the focal point position information of the shooting device is determined based on the image position information of the plurality of second preset mark points in the image coordinate system, the calibration position information in the calibration coordinate system, and the first conversion relationship.

Optionally, in step S4, the step of adjusting the pointing structure so that the pointing direction of the pointing structure is matched with the surgical guide path corresponding to the virtual path includes:

obtaining locating position information of the surgical guide path in the locating coordinate system according to perspective coordinate information of the target spot path and the second conversion relationship; and adjusting the pointing structure according to the locating position information of the surgical guide path and locating position information of the pointing structure in the locating coordinate system, so that the pointing direction of the pointing structure coincides with an extending direction of the surgical guide path.

Optionally, the pointing structure includes a beam emitting component;

in step S3, a light beam emitted from the beam emitting component points to the target spot; and in step S4, the light beam emitted from the beam emitting component is matched with the target spot path;

alternatively, the pointing structure includes an instrument guide channel;

in step S3, a central axis of the instrument guide channel points to the target spot; and in step S4, the central axis of the instrument guide channel is matched with the target spot path.

Optionally, the system for determining the target spot path further includes a projection device, and in step S4, the method further includes:

obtaining a third conversion relationship between a projection coordinate system based on the projection device and the perspective coordinate system; and determining projection position information of the affected part in the projection coordinate system according to the three-dimensional partial image, the three-dimensional posture information of the virtual path, and the third conversion relationship, so as to perform projection according to the projection position information.

Optionally, the step of obtaining the third conversion relationship between the projection coordinate system based on the projection device and the perspective coordinate system includes:

obtaining, by the projection device, projection position information of the third preset mark points in the locating device in the projection coordinate system; and determining the third conversion relationship between the projection coordinate system and the perspective coordinate system according to the projection position information of the third preset mark points and locating coordinate information of the third preset mark points in the locating coordinate system.

Optionally, if the pointing structure includes an instrument guide channel, the method further includes:

obtaining locating position information of the instrument guide channel in the locating coordinate system, and obtaining projection position information of the instrument guide channel in the projection coordinate system according to the first conversion relationship and the third conversion relationship, so as to perform projection according to the projection position information of the instrument guide channel.

Optionally, the pointing structure is adjusted according to locating position information of the pointing structure in the locating coordinate system, the focal point position information, the first conversion relationship, the second conversion relationship, and position information of projected target spots in the image coordinate system, so that the pointing direction of the pointing structure points to the target spots in vivo.

The technical solutions provided by the embodiments of the present application may have the following advantageous effects:

When the simulated two-dimensional image is matched with the two-dimensional projection image, the present application can determine the perspective coordinate information of the target spot path through the three-dimensional posture information of the virtual path, so as to assist medical staff in introducing the instrument and improve the accuracy of surgery; moreover, the locating device is separate from the shooting device in the present application, so that the shooting device can be removed after the first conversion relationship is determined, and the target spot path can be determined through the locating device, which avoids the occupation of surgical space by the shooting device and makes more room for the medical staff to perform operations.

The shooting device and the locating device in the present application are independent from each other. Locating balls on the calibration device and the locating device are used for identification and for obtaining a relative position relationship, so that the shooting device can be removed after the relative position relationship is determined. The locating device can adjust the pointing structure according to the relative position relationship and the conversion relationship between the coordinate systems so that the pointing structure points to the target spots in vivo, thereby realizing the locating of the target spots in vivo, while also avoiding occupation of the space by the shooting device.

The present application obtains the three-dimensional posture parameters of the three-dimensional partial image when the simulated two-dimensional image is matched with the two-dimensional image, thereby obtaining the perspective position information of the affected part when based on the shooting device; further, the perspective position information is converted to the projection coordinate system through the coordinate conversion relationship for projection, so that the medical staff can project the affected part to any suitable position according to needs, which is advantageous for observing the operation process at any time and realizing non-invasive real-time projection. In particular, the projection on the virtual path can provide assistance to the medical staff in insertion of the needle, which is helpful for improving the accuracy of the operation.

In the present application, physical posture parameters, which are based on the shooting device, of the surgical path in the affected part is obtained by matching the simulated two-dimensional image with the two-dimensional projection image, so that the pointing structure can be adjusted according to the physical posture parameters to sequentially point to a plurality of target spots constituting the surgical path. Based on this, a planned route on the body surface that corresponds to the surgical path can be obtained. The planned route can assist the medical staff in implanting surgical instruments and assist in path planning during the operation, which is advantageous for improving the accuracy of the operation and relieving the pain of the patient.

By matching the simulated two-dimensional image with the two-dimensional projection image, and determining path information in the two-dimensional projection image according to the projection of the virtual path in the simulated two-dimensional image in a case where it is confirmed that the simulated two-dimensional image is matched with the two-dimensional projection image, the present application enables the medical staff to intuitively learn the path information so that the medical staff is assisted in determining the current needle entry point and needle entry angle, which is advantageous for improving the accuracy of the operation and relieving the pain of the patient.

It should be understood that the above general description and the following detailed description are only illustrative and exemplary, and cannot limit the present application.

DETAILED DESCRIPTION OF THE INVENTION

The present disclosure will be described in detail below with reference to the accompanying drawings and specific embodiments. Not all the embodiments will not be described in great detail herein, but the embodiments of the present disclosure are not therefore limited to the following embodiments.

Figure 1:
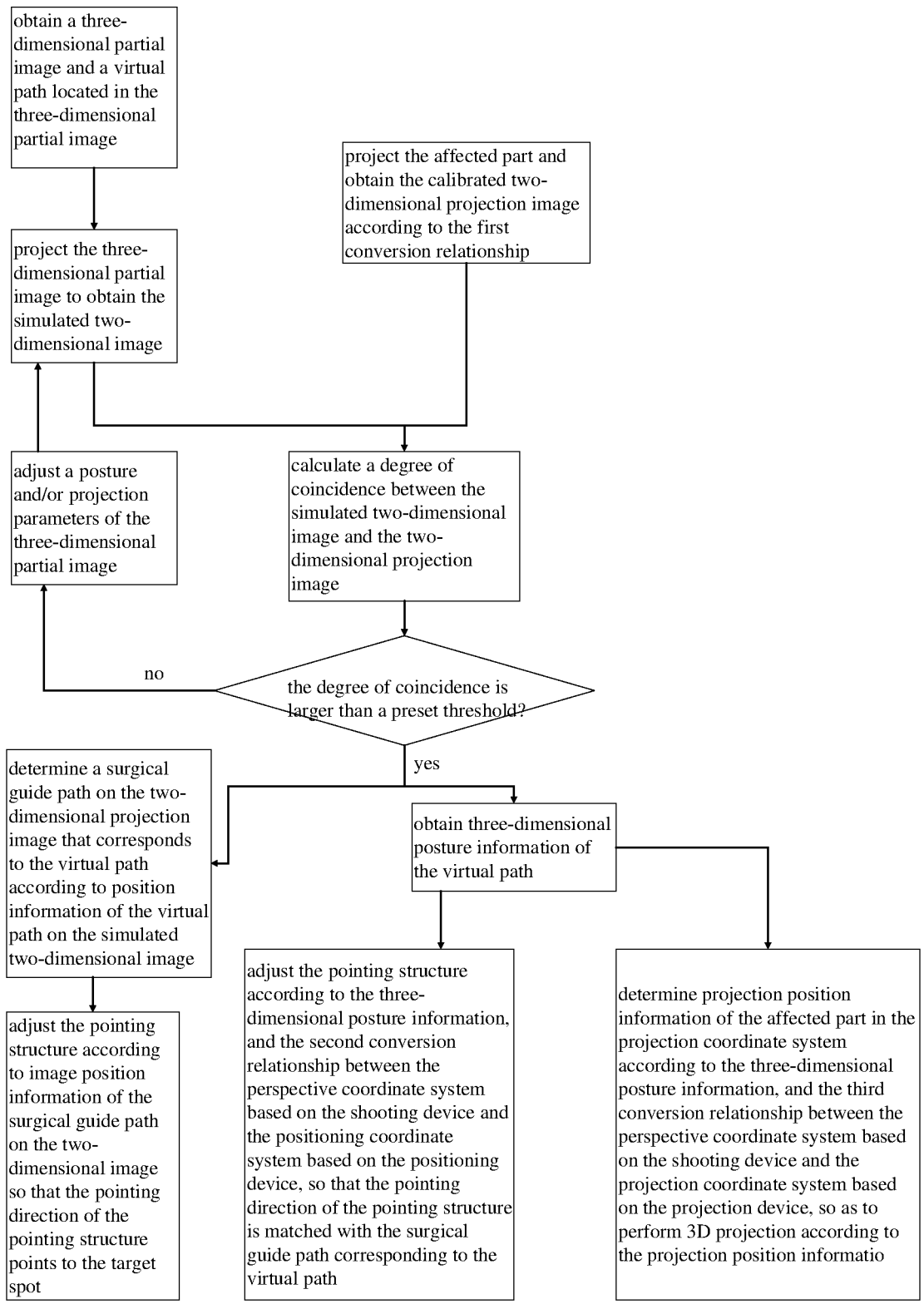
FIG. 1 is a flowchart of a method for determining a target spot path of the present disclosure.
Figure 2:
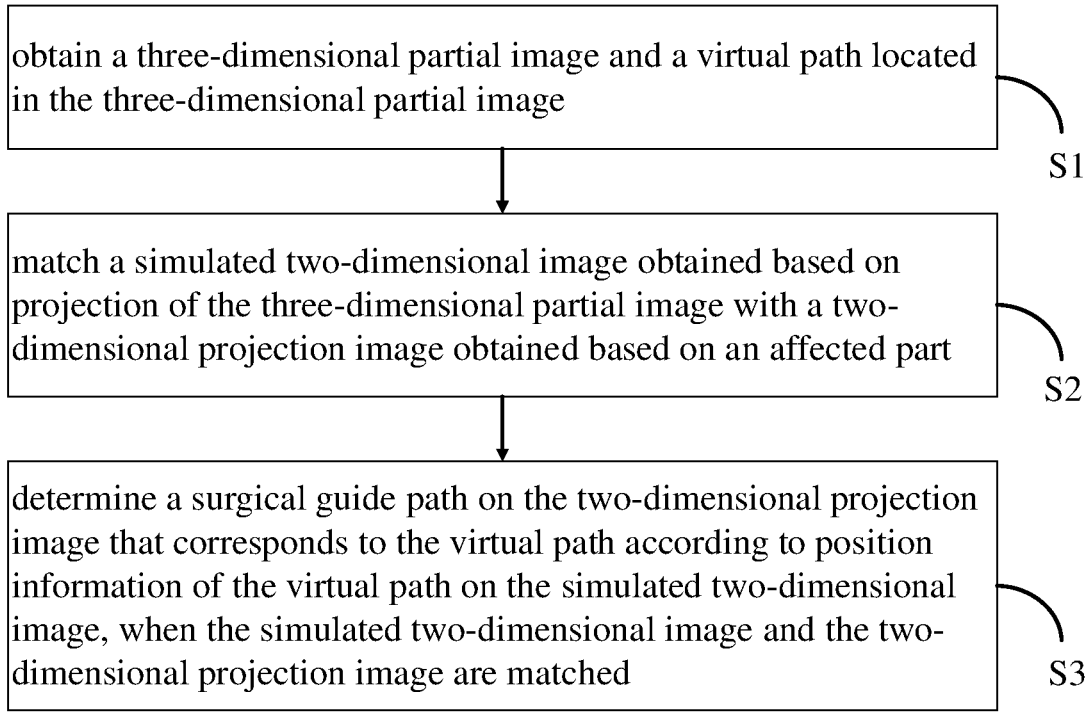
FIG. 2 is a block diagram showing steps of a method for determining a target spot path according to an exemplary embodiment.

As shown in FIG. 1 and FIG. 2, the method for determining a path of the present disclosure may include the following steps.

In step S1, a three-dimensional partial image for an affected part and a virtual path located in the three-dimensional partial image are obtained.

This step includes:

S11. reconstructing the three-dimensional partial image based on scanned information; and S12. obtaining the virtual path located in the three-dimensional partial image.

In this embodiment, scanned information can be obtained through CT scanning or MR images, and the scanned information can be input into a computer for reconstructing and obtaining a three-dimensional partial image. A virtual path can be established for the affected part according to a current state of the affected part shown in the three-dimensional partial image. The affected part in this embodiment may include limbs, spine, waist, chest, or head, etc., and no limitations are imposed to the affected part herein. The virtual path may be linear, and the length, width, and angle of the virtual path may be adjusted in the three-dimensional partial image. Specifically, they are adjusted in accordance with the specifications of the implanted devices, and the implanted devices may include steel nails and the like.

In step S2, a simulated two-dimensional image obtained based on projection of the three-dimensional partial image is matched with a two-dimensional projection image obtained based on the affected part.

In this embodiment, a C-arm machine or other X-ray imaging equipment can be used to shoot the affected part to obtain a two-dimensional projection image point. A simulated two-dimensional image and position information of the virtual path in the simulated two-dimensional image can be obtained through the DRR algorithm based on the three-dimensional partial image. Further, a degree of coincidence between the two-dimensional projection image and the simulated two-dimensional image can be determined, and if the degree of coincidence is not smaller than a preset threshold, it can be considered that the two-dimensional projection image is matched with the simulated two-dimensional image.

Further, if the degree of coincidence between the two-dimensional projection image and the simulated two-dimensional image is smaller than the preset threshold, it can be considered that the difference between the two-dimensional projection image and the simulated two-dimensional image is relatively large at this time; then, an adjusted simulated two-dimensional image can be obtained by adjusting a spatial posture of the three-dimensional partial image or adjusting projection parameters for the three-dimensional partial image, and the adjusted simulated two-dimensional image is matched with the two-dimensional projection image.

Specifically, in an embodiment, the difference between the simulated two-dimensional image and the two-dimensional projection image may be fed back according to the degree of coincidence between the simulated two-dimensional image and the two-dimensional projection image, so that the spatial posture of the three-dimensional partial image or the projection parameters for the three-dimensional partial image are adjusted according to the degree of coincidence.

Of course, in the process of matching the simulated two-dimensional image with the two-dimensional projection image, the spatial posture of the three-dimensional partial image and the projection parameters for the three-dimensional partial image may also be adjusted simultaneously. Furthermore, when the simulated two-dimensional image obtained based on the projection of the three-dimensional partial image is matched with the two-dimensional projection image obtained based on the affected part, the three-dimensional posture information of the virtual path is obtained. The spatial posture of the three-dimensional partial image or the projection parameters is sequentially adjusted at regular intervals.

In this embodiment, when the simulated two-dimensional image is matched with the two-dimensional projection image, it means that the three-dimensional posture parameters of the three-dimensional partial image at this time are perspective position information of the affected part relative to a perspective coordinate system of the shooting device. At this time, the three-dimensional posture information of the virtual path may be used as the perspective position information of the surgical path to be established at the affected part in the perspective coordinate system.

Specifically, perspective projection may be performed on the affected part to obtain the two-dimensional projection image, the three-dimensional partial image may be projected to obtain the simulated two-dimensional image, and the degree of coincidence of the simulated two-dimensional image and the two-dimensional projection image may be obtained; if the coincidence degree is not smaller than the preset threshold, it is determined that the simulated two-dimensional image is matched with the two-dimensional projection image. For example, the difference between the simulated two-dimensional image and the two-dimensional projection image may also be fed back according to the degree of coincidence between the simulated two-dimensional image and the two-dimensional projection image, so that the spatial posture of the three-dimensional partial image and/or the projection parameters for the three-dimensional partial image are adjusted according to the degree of coincidence. Of course, in other embodiments, the spatial posture of the three-dimensional partial image or the projection parameters is sequentially adjusted at regular intervals, to which the present application does not impose any limitation.

Adjusting the spatial posture of the three-dimensional partial image may be adjusting a rotational angle of the three-dimensional partial image with respect to at least one coordinate axis, or adjusting a displacement of the three-dimensional partial image with respect to at least one coordinate axis. Of course, in other embodiments, it is also possible to adjust both the rotational angle and displacement with respect to any coordinate axis. Adjusting the projection parameters for the three-dimensional partial image may be adjusting one or more parameters of a position of a virtual light source, a focal length of the virtual light source, and an imaging resolution. The imaging resolution is used to characterize the relationship between pixel and geometric size, and it is related to a size of a projection imaging plane of the three-dimensional partial image and an image size of the two-dimensional projection image.

In each of the foregoing embodiments, the degree of coincidence between the simulated two-dimensional image and the two-dimensional projection image may be implemented in the following manners.

In an embodiment, the degree of coincidence may be obtained by matching the two-dimensional projection image with the simulated two-dimensional image by the user.

In another embodiment, a first projection area in the simulated two-dimensional image and a second projection area in the two-dimensional projection image may be extracted, and the degree of coincidence is obtained according to a degree of edge contour matching between the first projection area and the second projection area.

In another embodiment, both the simulated two-dimensional image and the two-dimensional projection image may be segmented in a preset direction according to a preset ratio, and each segmented area of the simulated two-dimensional image is matched with a corresponding segmented area of the two-dimensional projection image to obtain the degree of coincidence.

In step S3, when the simulated two-dimensional image is matched with the two-dimensional projection image, a surgical guide path on the two-dimensional projection image that corresponds to the virtual path is determined according to position information of the virtual path on the simulated two-dimensional image.

In this embodiment, when the simulated two-dimensional image is matched with the two-dimensional projection image, it can be considered that the posture information of the three-dimensional partial image at this time can be used as the perspective position information of the affected part based on the perspective coordinate system of the shooting device, so that at this time the position information of the virtual path in the three-dimensional partial image in the simulated two-dimensional image can be used as the posture information of the surgical path in the two-dimensional projection image, thereby obtaining the surgical path in the two-dimensional projection image, which is helpful for the medical staff to learn the needle entry point and needle entry angle of the surgical instrument and which is further helpful for improving the accuracy of the operation and relieving the pain of the patient.

Figure 3:
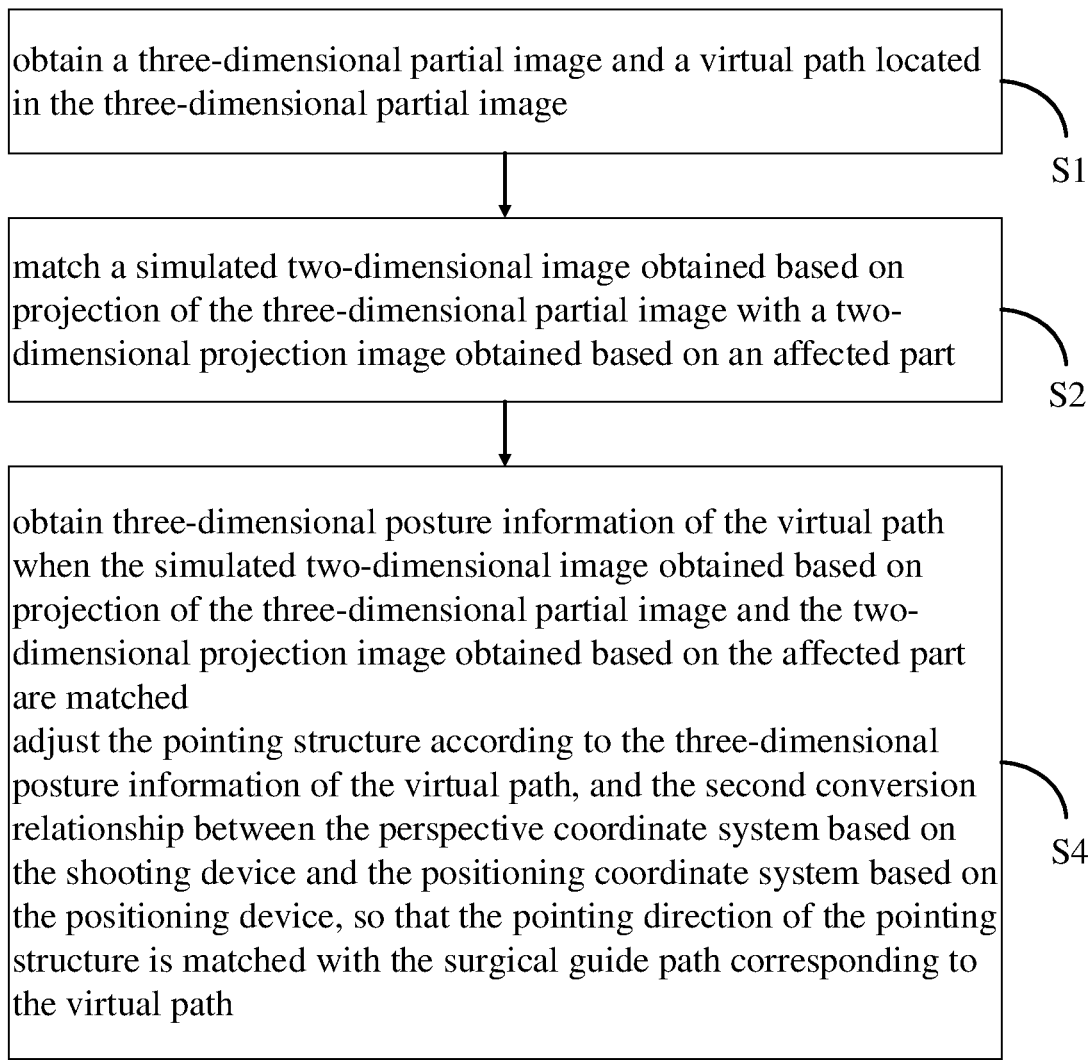
FIG. 3 is a block diagram showing steps of another method for determining a target spot path according to an exemplary embodiment.

After step S3, the method for determining the path of the present disclosure may optionally include the following step S4. Specifically, FIG. 3 is a flowchart of a method for determining the path according to another exemplary embodiment. As shown in FIG. 1 and FIG. 3, in step S4, when the simulated two-dimensional image is matched with the two-dimensional projection image, the three-dimensional posture information of the virtual path on the three-dimensional partial image is obtained as the perspective coordinate information of the surgical guide path based on the perspective coordinate system, in which the perspective coordinate system is formed based on the shooting device.

According to a second conversion relationship between the perspective coordinate information of the surgical guide path, the perspective coordinate system and the locating coordinate system based on the locating device, the pointing structure is adjusted so that the pointing direction of the pointing structure is matched with the surgical guide path corresponding to the virtual path.

In this embodiment, the three-dimensional posture information of the virtual path is the perspective position information of the surgical path to be established in the affected part relative to the perspective coordinate system on the shooting device, and according to the second conversion relationship, the locating position information of the surgical path in the locating coordinate system can be obtained. The pointing structure is located on the locating device, so that the locating position information of the pointing structure relative to the locating coordinate system is known; therefore, the locating position information of the surgical path in the locating coordinate system and the locating position information of the pointing structure relative to the locating coordinate system can be used to adjust the pointing structure, so that the pointing direction of the pointing structure is matched with the virtual path.

It should be pointed out that according to the above solution, in the method for determining the path of the present disclosure, step S4 may also be executed simultaneously with the execution of step S3, and the execution process is the same as the above steps, so it will not be repeated herein.

Figure 4:
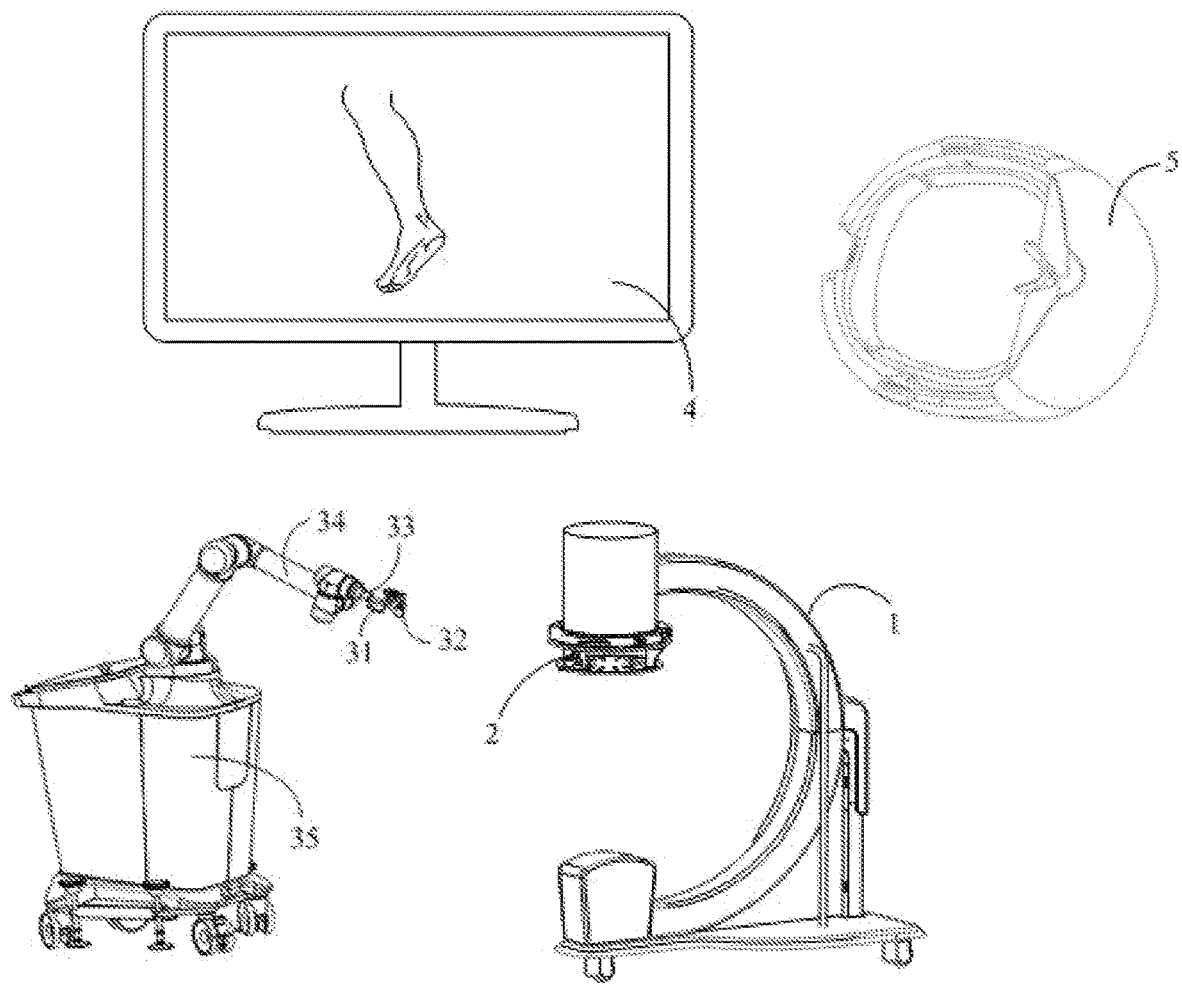
FIG. 4 is a schematic structural diagram showing a determining system according to an exemplary embodiment.

In order to further illustrate the present disclosure, based on the above technical solution of the present application, a determining system applied to the determining method is provided. As shown in FIG. 4, the determining system may include a shooting device 1, a calibration device 2, a locating device 3, a display device 4, an optional two-dimensional locating device (not shown in the figure) and a projection module 5. The locating device 3 is physically separate from the shooting device 1, and the locating device 3 may include a pointing structure 31. In this embodiment, the shooting device can be used to shoot the affected part to obtain a two-dimensional projection image. In this embodiment, the calibration device 2 is connected to the shooting device 1, and projection light emitted from the shooting device 1 passes through the calibration device 2. The above-mentioned second conversion relationship can be obtained through a locating coordinate system of the locating device 3 and a perspective coordinate system based on the shooting device 1, and the display device can be connected and communicated to the shooting device in a wired or wireless manner. The display device may also include a display screen which may be used to show related images such as a three-dimensional partial image, a two-dimensional projection image, and a simulated two-dimensional image. The computer may also include a processor (not shown in the figure) and a memory for storing instructions executable by the processor. In this embodiment, the projection module 5 determines the projection position information of the affected part in the projection coordinate system according to the three-dimensional partial image, the three-dimensional posture information of the virtual path and the third conversion relationship, so as to perform projection according to the projection position information.

In each of the following embodiments, the coordinate system established based on the shooting device 1 is identified as a perspective coordinate system, the coordinate system established based on the calibration device 2 is identified as a calibration coordinate system, the coordinate system established based on the locating device 3 is identified as a locating coordinate system, and the coordinate system in the projection image obtained based on the shooting device 1 is identified as an image coordinate system.

Figure 12:
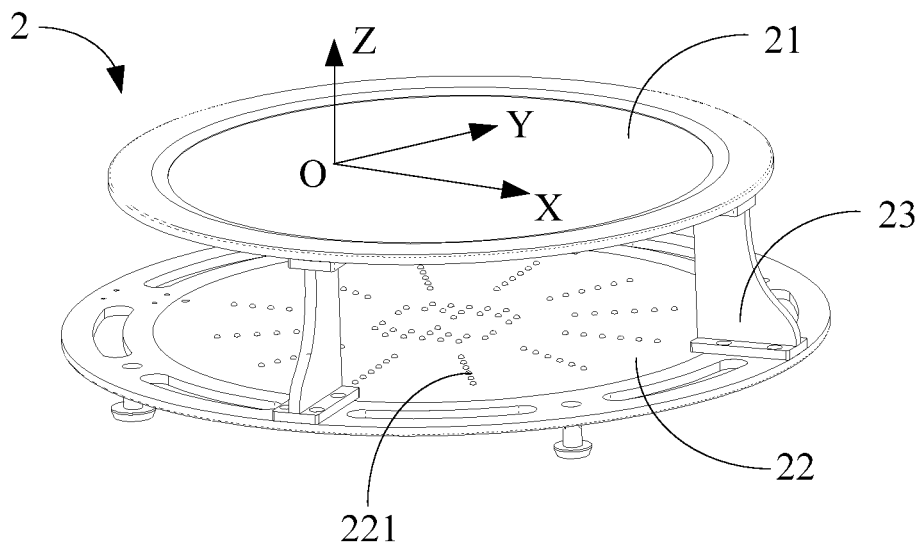
FIG. 12 is a schematic structural diagram of a calibration device according to an exemplary embodiment.

As shown in FIG. 4 and FIG. 12, in this embodiment, the light emitted from the shooting device 1 passes through the calibration device 2, so that a projection image of the calibration device 2 is obtained, and a first conversion relationship between focal point position information of the shooting device 1, the image coordinate system and the calibration coordinate system is determined according to image position information of each preset point in the projection image of the calibration device 2 in the image coordinate system, and calibration position information of the preset point in the calibration coordinate system. In this embodiment, the calibration device 2 includes a calibration plate 21 and a first identification plate 22, the calibration plate 21 includes a plurality of first locating balls, and the first identification plate 22 includes a plurality of second locating balls 221.

In this embodiment, the locating device 3 includes a second identification plate 31 and a beam emitting structure 32. The second identification plate 31 includes a plurality of third locating balls, and the plurality of third locating balls are used to determine a second conversion relationship between the locating coordinate system and the perspective coordinate system. The locating system also includes a computing device (not shown in the figure), which can generate an adjustment instruction based on the focal point position information, the first conversion relationship, the second conversion relationship, the image coordinate information of the target spots in the image coordinate system and the position information of the pointing structure in the locating coordinate system, and the adjustment instruction is used to adjust the pointing structure so that the pointing structure points to the target spots.

In this embodiment, the pointing structure includes a beam emitting component. Light emitted from the beam emitting component is directed to the target spots in vivo, and position information of the light beam can be positioned later to adjust a guide channel; or the pointing structure may also include an instrument guide channel, and surgical instruments can be positioned through the instrument guide channel; or the locating device 3 may also include the beam emitting component and the instrument guide channel at the same time.

Further, in order to facilitate the operation, the locating device 3 may also include a mechanical arm 34 connected to a clamping structure 33, so that when the mechanical arm 34 drives the clamping structure 33 to move or rotate, the second identification plate 31 and the pointing structure 32 can move or rotate synchronously, thus enabling the position of the pointing structure 32 to be moved so that the light emitted from the pointing structure 32 is directed to the target spots in vivo (the specific process will be described in detail later).

Furthermore, in order to increase the operable range of the mechanical arm 34, the locating device 3 may further include a sliding base 35. The sliding base 35 may be of a trolley structure, and a shelf may be provided on the sliding base 35 for placing other auxiliary structures.

According to an embodiment of the present disclosure, when the two-dimensional projection image is matched with the simulated two-dimensional image, the posture parameters of the three-dimensional partial image may be used as the physical posture parameters of the affected part based on the shooting device. Therefore, the posture parameters of the virtual path may be used as the physical posture parameters of the actual surgical path based on the shooting device. Therefore, according to the image position information of a plurality of position points on the virtual path on the simulated two-dimensional image, the pointing structure can be adjusted so that the pointing direction of the pointing structure sequentially points to the corresponding target spots in the affected part.

In an embodiment, the determining method of the present disclosure based on the above determining system can be applied to determine the target spot path on the perspective image. In the application process, a two-dimensional locating device is installed on the shooting device 1 of the determining system. In this embodiment, the calibration device 2 is removed, and then the two-dimensional locating device is installed at the position where the calibration device 2 was installed on the shooting device 1. The two-dimensional locating device has the same double-layer plate structure as the calibration device 2, and the interval between the two plates of the two-dimensional locating device is the same as the interval between the two plates of the calibration device 2. Therefore, based on the first preset mark points (i.e., the first locating balls) and the second preset mark points (i.e., the second locating balls 221) that are arranged at intervals from each other in the projection direction on the original calibration device 2, the determining system can obtain the image position information of each of the first preset mark points and each of the second preset mark points in the image coordinate system which is formed based on a projection image of the two-dimensional locating device that has replaced the calibration device 2; according to the image position information of the plurality of first preset mark points in the image coordinate system, the locating coordinate information of the plurality of first preset mark points in the locating coordinate system of the two-dimensional locating device, and the image position information of each position point in the image coordinate system, the locating coordinate information of the first locating point based on the locating coordinate system is determined, in which the first locating point and the corresponding position point coincide in the image coordinate system; according to the image position information of the plurality of second preset mark points in the image coordinate system, the locating coordinate information of the plurality of second preset mark points in the locating coordinate system of the two-dimensional locating device, and the image position information of each position point in the image coordinate system, the locating coordinate information of the second locating point based on the locating coordinate system is determined, in which the second locating point and the corresponding position point coincide in the image coordinate system; the pointing structure is adjusted according to the locating position information of the first locating point and the locating position information of the second locating point.

In another embodiment, the image position information of the projection path on the two-dimensional projection image that is matched with the virtual path can be obtained through the image position information of the virtual path on the simulated two-dimensional image, and the pointing structure can be further adjusted according to the image position information of a plurality of position points on the projection path.

Each of the foregoing embodiments may further include calibrating the two-dimensional projection image. For example, the first conversion relationship between the locating coordinate system and the image coordinate system may be determined according to the locating position information of the plurality of third preset mark points in the locating coordinate system and the image coordinate information of the plurality of third preset mark points in the image coordinate system. According to the first conversion relationship, a calibrated two-dimensional projection image is obtained to reduce image distortion and deformation and improve the accuracy of the pointing structure pointing to the target spots.

Following the above overall general description of the solution of the present disclosure, the following embodiments are used to further illustrate the solution of the present disclosure.

First Embodiment

Figure 5:
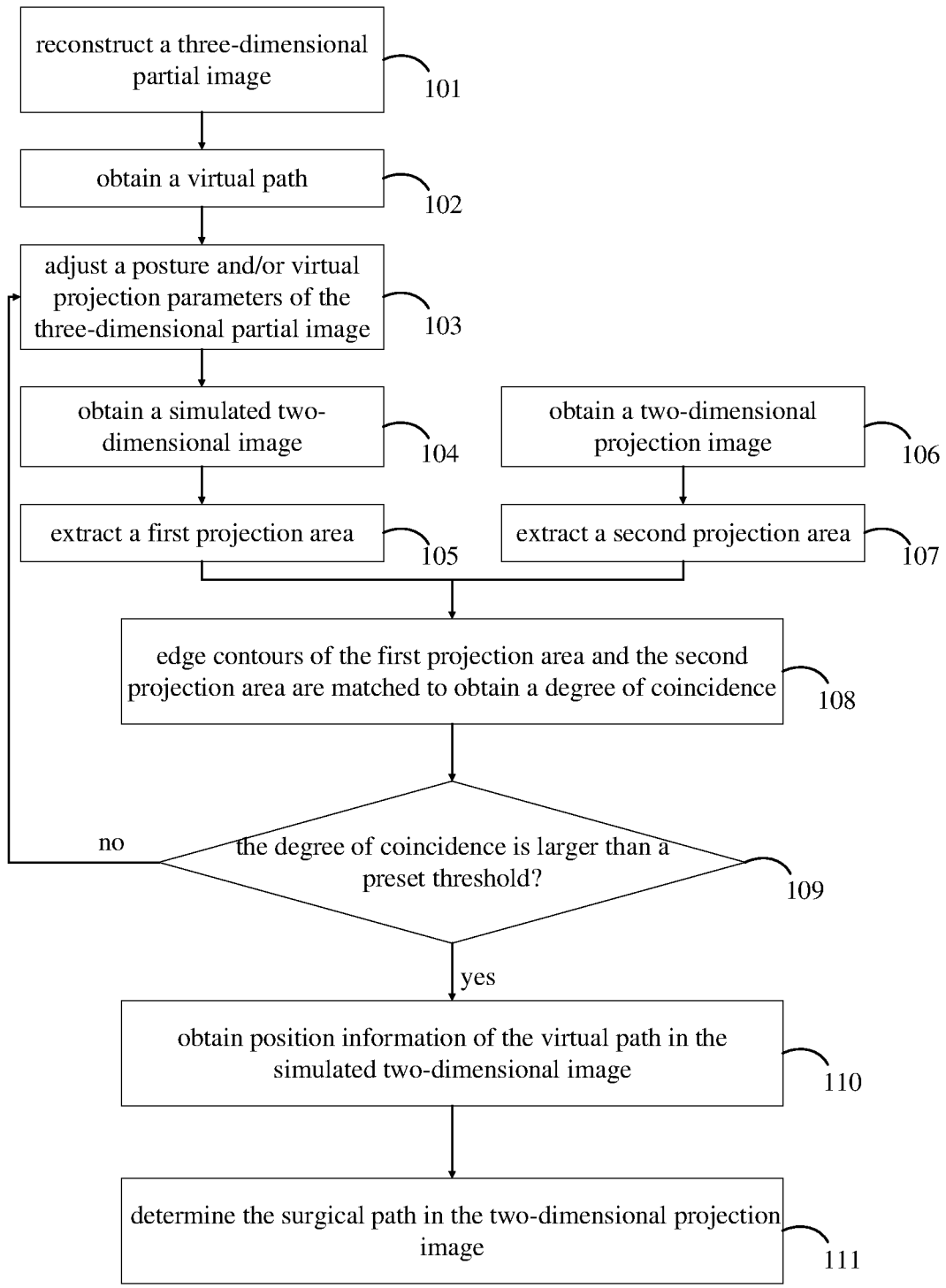
FIG. 5 is a flowchart of a method for determining a target spot path according to an exemplary embodiment.

As shown in FIG. 5, the process of determining the surgical guide path on the two-dimensional projection image that corresponds to the virtual path may include the following steps.

In step 101, a three-dimensional partial image is reconstructed according to scanned information.

In step 102, a virtual path located in the three-dimensional partial image is obtained. The way of obtaining the virtual path is as described above, and will not be repeated herein.

In step 103, a spatial posture and/or projection parameters of the three-dimensional partial image are adjusted. The adjustment manner is as described above, and will not be repeated herein.

In step 104, projection is performed on the three-dimensional partial image to obtain a simulated two-dimensional image.

In step 105, a first projection area is extracted based on the simulated two-dimensional image.

In step 106, an affected part is shot to obtain a two-dimensional projection image.

In step 107, a second projection area is extracted based on the two-dimensional projection image.

In this embodiment, based on the size of a projection plane and an area covered by the virtual light source, in addition to the area corresponding to the three-dimensional partial image, there are inherently other areas in the simulated two-dimensional image. Similarly, in the two-dimensional projection image, in addition to an area corresponding to the lesion, there may be other areas. Therefore, in the present application, the first projection area in the simulated two-dimensional image and the second projection area in the two-dimensional projection image are extracted through image processing. The image processing may be extracting a disease area in the simulated two-dimensional image and a disease area in the two-dimensional projection image based on gray value.

In step 108, edge contours of the first projection area and the second projection area are matched to obtain a degree of coincidence.

In this embodiment, the edge contours of the first projection area and the second projection area may be matched to obtain the degree of coincidence between the two-dimensional projection image and the simulated two-dimensional image. For example, based on a mark point on the first projection area and a corresponding position of the mark points on the second projection area, a relative position of the first projection area and the second projection area may be adjusted so that the mark point and the corresponding position of the mark point on the second projection area basically coincide, and then edge contour matching is performed. The mark point may be a special area on the affected part, such as a nerve mark point, a bone mark point, etc., to which present application does not impose any limitation.

In step 109, it is determined whether the degree of coincidence is larger than a preset threshold.

In this embodiment, if the degree of coincidence between the two-dimensional projection image and the simulated two-dimensional image is larger than or equal to the preset threshold, step 110 is executed, and if the degree of coincidence between the two-dimensional projection image and the simulated two-dimensional image is smaller than the preset threshold, step 103 is executed. The adjustment amount and adjustment direction for the spatial posture of the three-dimensional partial image and for the projection parameters may be determined according to the degree of coincidence, so as to improve the matching efficiency.

In step 110, position information of the virtual path in the simulated two-dimensional image is obtained.

In step 111, according to the position information of the virtual path in the simulated two-dimensional image, position information of the surgical path (that is, the surgical guide path) in the two-dimensional projection image is determined.

In this embodiment, the degree of coincidence between the simulated two-dimensional image and the two-dimensional projection image is already larger than or equal to the preset threshold. Therefore, based on the projection information of the virtual path in the simulated two-dimensional image, the position information of the surgical path on the two-dimensional partial image can be determined, and the needle entry point and needle entry direction can be obtained.

Figure 6:
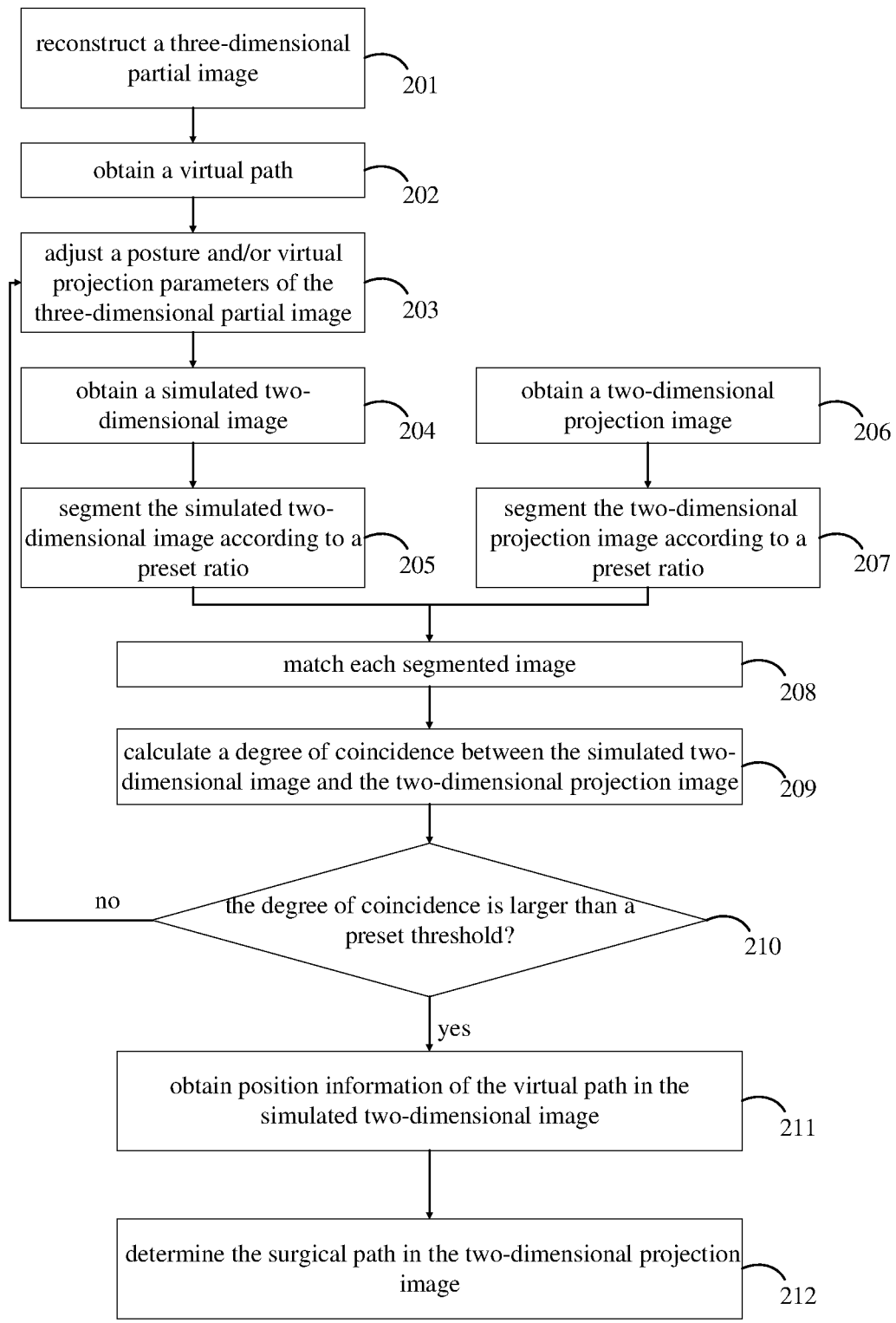
FIG. 6 is a flowchart of another method for determining a target spot path according to an exemplary embodiment.

As shown in FIG. 6, for the above solution, a detailed description will be given below based on another specific embodiment. In steps S1 to S3, the process of determining the surgical guide path on the two-dimensional projection image that corresponds to the virtual path may include the following steps:

In step 201, a three-dimensional partial image is reconstructed according to scanned information.

In step 202, a virtual path located in the three-dimensional partial image is obtained.

In step 203, a spatial posture and projection parameters of the three-dimensional partial image are adjusted.

In step 204, projection is performed on the three-dimensional partial image to obtain a simulated two-dimensional image.

In this embodiment, for steps 201-204, reference may be made to steps 101-104 in the embodiment shown in FIG. 5, and a repeated description is omitted herein.

In step 205, the simulated two-dimensional image is segmented in a preset direction according to a preset ratio.

In step 206, an affected part is shot to obtain a two-dimensional projection image.

In step 207, the two-dimensional projection image is segmented in a preset direction according to a preset ratio.

Figure 7:
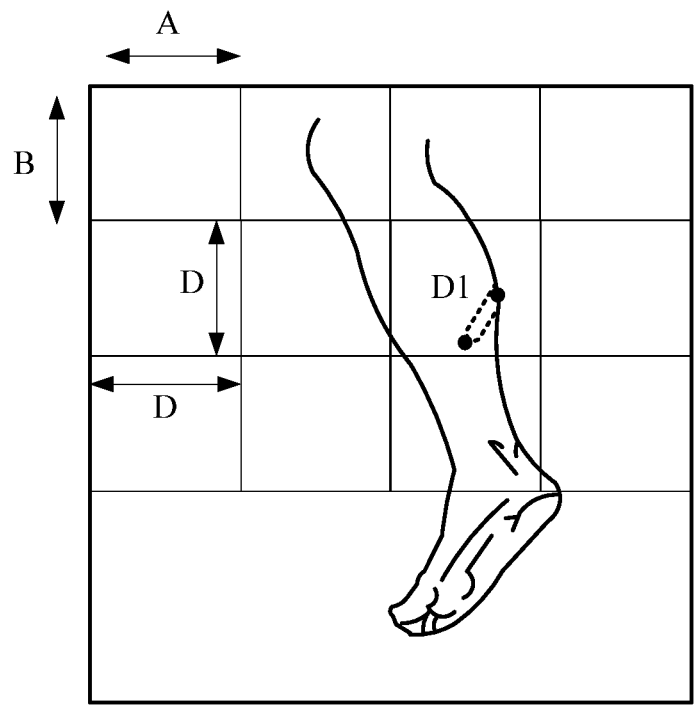
FIG. 7 is a schematic diagram showing a simulated two-dimensional image according to an exemplary embodiment.
Figure 8:
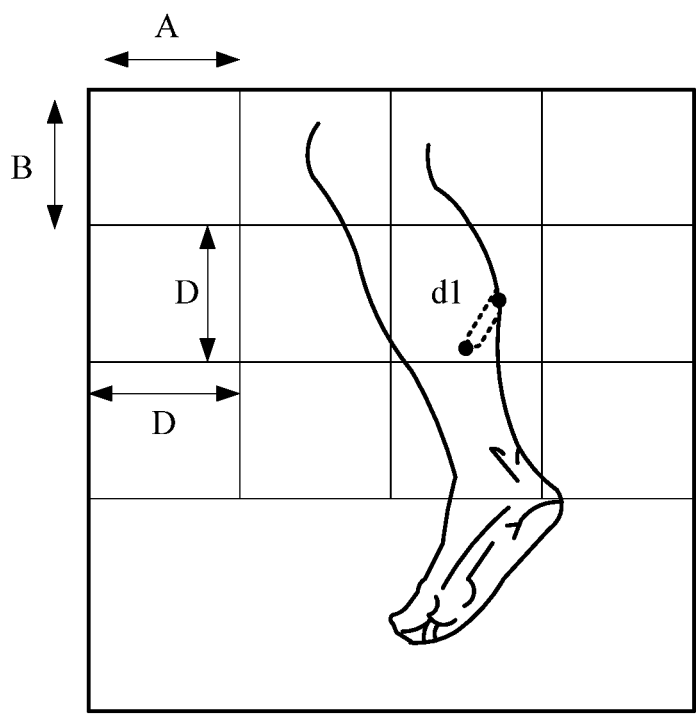
FIG. 8 is a schematic diagram showing a two-dimensional projection image according to an exemplary embodiment.

In this embodiment, as shown in FIGS. 7 and 8, the simulated two-dimensional image of FIG. 7 and the two-dimensional image of FIG. 8 may be segmented in rows and columns in the direction indicated by arrow A and the direction indicated by arrow B to obtain N segmented areas with a size of D×D respectively.

In step 208, each segmented image of the simulated two-dimensional image is matched with the segmented image of a corresponding area on the two-dimensional projection image.

In step 209, according to the matching result, a degree of coincidence between the simulated two-dimensional image and the two-dimensional projection image is calculated.

In this embodiment, as shown in FIGS. 7 and 8, each segmented area in FIG. 7 has a corresponding area in FIG. 8. For example, the segmented area D1 in the second row and third column in FIG. 7 corresponds to the segmented area d1 in the second row and third column of FIG. 8, and the segmented areas D1 and d1 can be further matched to obtain a matching value. Similarly, other segmented areas in FIG. 7 can be matched with the corresponding segmented areas in FIG. 8 to finally obtain the degree of coincidence. For example, each segmented area may correspond to a weighting coefficient, and the sum of the product of the matching degree and the weighting coefficient of each segmented area and the products of the matching degrees and the weighting coefficients of other segmented areas is the degree of coincidence.

In step 210, it is determined whether the degree of coincidence is larger than a preset threshold.

In this embodiment, if the degree of coincidence between the two-dimensional projection image and the simulated two-dimensional image is larger than or equal to the preset threshold, step 211 is executed, and if the degree of coincidence between the two-dimensional projection image and the simulated two-dimensional image is smaller than the preset threshold, step 203 is executed.

In step 211, position information of the virtual path in the simulated two-dimensional image is obtained.

In step 212, according to the position information of the virtual path in the simulated two-dimensional image, a surgical path (that is, a surgical guide path) pointing to target spots in the two-dimensional projection image is determined.

In this embodiment, for steps 211 and 212, reference may be made to steps 110 and 111 in the embodiment shown in FIG. 5, and a repeated description is omitted herein.

Second Embodiment

Figure 9:
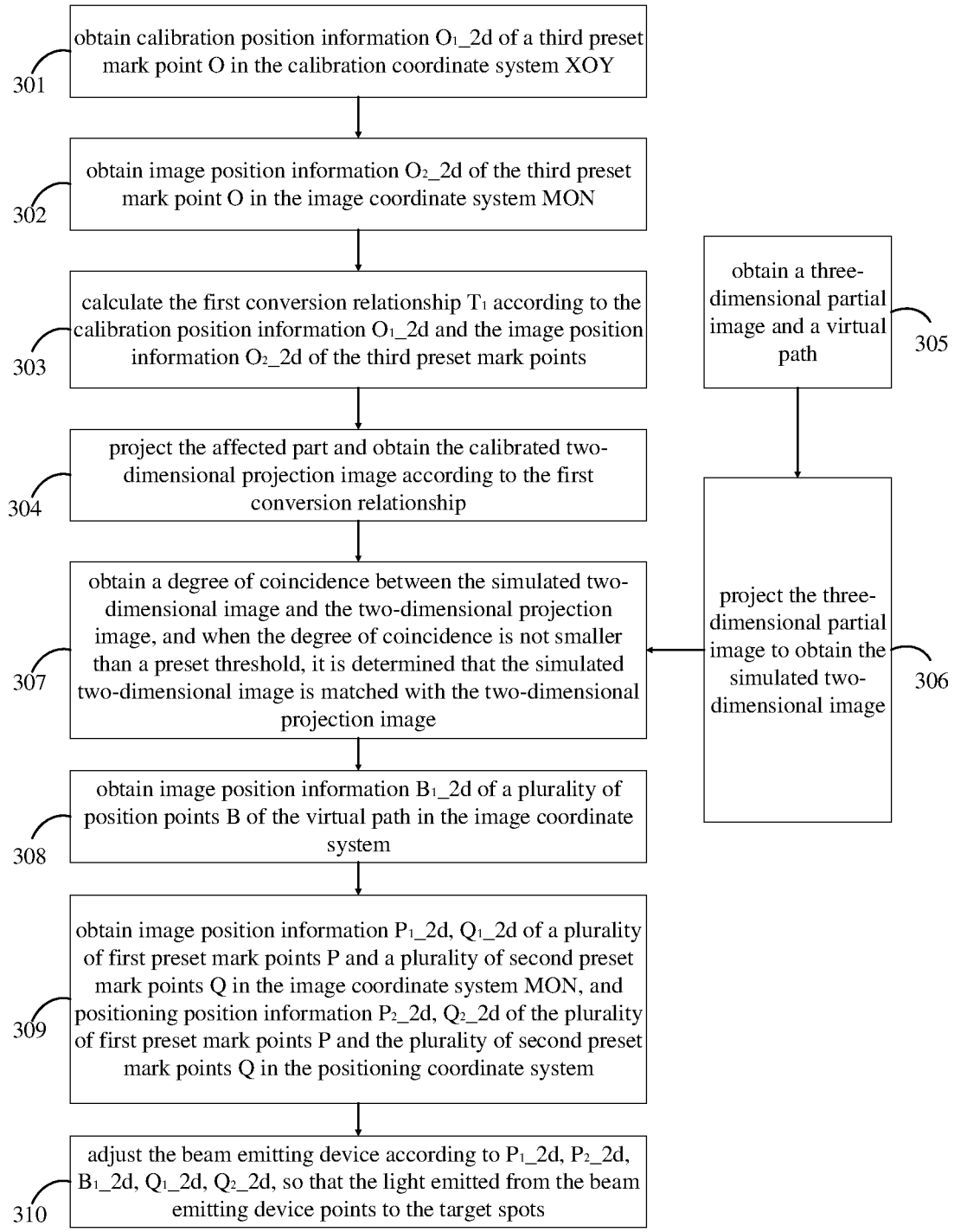
FIG. 9 is a flowchart for assisting in locating a target spot according to an exemplary embodiment.

As shown in FIG. 9, the process of the auxiliary method for determining the target spot may include the following steps.

In step 301, calibration position information $O_1\_2d$ of a first preset mark point O in the calibration coordinate system XOY is obtained.

In this embodiment, the image shot by the C-arm machine can be calibrated by a preset calibration device, and the preset calibration device can be provided with a plurality of first preset mark points. The calibration coordinate system is located at any position on the preset calibration device, and each of the first preset mark points is located on the calibration device, so that the calibration position information of each of the first preset mark points is known. In this embodiment, assuming that the origin is located on an upper surface of the calibration plate, then a calibration coordinate system XOY can be established based on an extending direction of the upper surface, and calibration position information of each of the first locating balls in the calibration coordinate system XOY can be obtained according to the physical structure sizes of the calibration plate itself. Here, the locating position information of the plurality of first preset mark points O may be expressed as $O_1\_2d$. Since there are a plurality of the first preset mark points, the locating position information $O_1\_2d$ may include O1 (X1, Y1), O2 (X2, Y2) ... (Xn, Yn), and the specific number is not limited by the present application.

In step 302, image position information $O_2\_2d$ when the distortion of the first preset mark point O occurs in the image coordinate system MON is obtained.

In this embodiment, the image coordinate system is formed based on the two-dimensional image obtained by the projection of the C-arm machine. When the C-arm machine shoots the calibration device to obtain the two-dimensional image, the two-dimensional image will include a plurality of projection points corresponding to the first preset mark points, and the image position information $O_2\_2d$ when the distortion of the plurality of projection points occurs in the image coordinate system MON is obtained. Similarly, since there are a plurality of the first preset mark points, the image position information $O_2\_2d$ when the distortion occurs may include O1 (M1, N1), O2 (M2, N2) ... (Mn, Nn), and the specific number is not limited by the present application.

In step 303, the first conversion relationship T1 between the calibration coordinate system XOY and the image coordinate system MON is calculated according to the calibration position information $O_1\_2d$ of the first preset mark points and the distorted image position information $O_2\_2d$ when the distortion occurs.

In step 304, the affected part is projected, and the calibrated two-dimensional projection image is obtained according to the first conversion relationship T1.

In this embodiment, a functional relationship between the calibration position information and the distorted image position information can be established through a mathematical method, and the first conversion relationship T1 can be solved according to the functional relationship.

For example, the following functional relationships can be established:

$$M = a_0 + a_1 X + a_2 Y + a_3 X^2 + a_4 XY + a_5 Y^2 + a_6 X^3 + a_7 X^2 Y + a_8 X Y^2 + a_9 Y^3 + \ldots$$

$$N = b_0 + b_1 X + b_2 Y + b_3 X^2 + b_4 XY + b_5 Y^2 + b_6 X^3 + b_7 X^2 Y + b_8 X Y^2 + b_9 Y^3 + \ldots$$

where (M, N) is the image position information when the distortion occurs, (X, Y) is the calibration position information, and $a_0 \ldots a_9$, $b_0 \ldots b_9$ is used to represent the first conversion relationship T1. In other words, the first conversion relationship T1 represents the conversion relationship between the distorted image and the undistorted image. Therefore, after the two-dimensional projection image of the affected part in a distorted state is obtained by shooting with the C-arm machine, calibration can be performed through the first conversion relationship, so as to obtain a calibrated two-dimensional projection image.

In step 305, a three-dimensional partial image and a virtual path located in the three-dimensional partial image are obtained.

In this embodiment, three-dimensional reconstruction can be performed based on the scanned information of the C-arm machine or the scanned information of other equipment, so as to obtain a three-dimensional partial image based on the affected part. Further, a virtual path can be established for the affected part according to the current state of the affected part shown in the three-dimensional partial image.

In step 306, the three-dimensional partial image is projected to obtain a simulated two-dimensional image.

In step 307, a degree of coincidence between the simulated two-dimensional image and the two-dimensional projection image is obtained, and when the degree of coincidence is not smaller than a preset threshold, it is determined that the simulated two-dimensional image is matched with the two-dimensional projection image.

In this embodiment, for the specific implementation of step 305 to step 307, reference may be made to the embodiment shown in FIG. 5 to FIG. 8.

In step 308, image position information $B1\_2d$ of a plurality of position points B of the virtual path in the image coordinate system is obtained.

In this embodiment, since the simulated two-dimensional image is matched with the calibrated two-dimensional projection image at this time, the image position information of each position point in the virtual path in the image coordinate system at this time can be used as the image position information of the corresponding point on the surgical path in the affected part in the calibrated two-dimensional projection image.

In step 309, image position information $P1\_2d$, $Q1\_2d$ of a plurality of first preset mark points P and a plurality of second preset mark points Q in the image coordinate system MON after the calibration, and locating position information $P2\_2d$, $Q2\_2d$ of the plurality of first preset mark points P and the plurality of second preset mark points Q in the locating coordinate system are obtained.

In this embodiment, the auxiliary method for a target spot path can be applied to an auxiliary system for determining a target spot path. The auxiliary system for determining a target spot path may include a locating device, and the locating device may include a plurality of first preset mark points P located on a first plane, a plurality of second preset mark points Q located on the first plane, and a pointing structure. In the projection direction, there is an interval between the first plane and the second plane.

Based on this, the locating position information of each locating mark point in the locating coordinate system formed based on the locating device can be obtained. Here, the locating position information of the plurality of first preset mark points P may be expressed as $P_2\_2d$, and the locating position information of the plurality of second preset mark points Q may be expressed as $Q_2\_2d$.

Further, the calibrated image position information $P_1\_2d$ of the first preset mark points P and the calibrated image position information $Q_1\_2d$ of the second preset mark points Q can be obtained based on the first conversion relationship T1 when the locating device is shot by the C-arm machine. The first preset mark points P and the second preset mark points Q are in different planes, so as to facilitate the subsequent construction of a straight line starting from the light source on the shooting device and pointing to the target spots according to the position information of the first preset mark points P and the second preset mark points Q in different planes.

In step 310, the beam emitting device is adjusted according to $P1\_2d$, $P2\_2d$, $B1\_2d$, $Q1\_2d$ and $Q2\_2d$, so that the light emitted from the beam emitting device points to the target spots.

Figure 10:
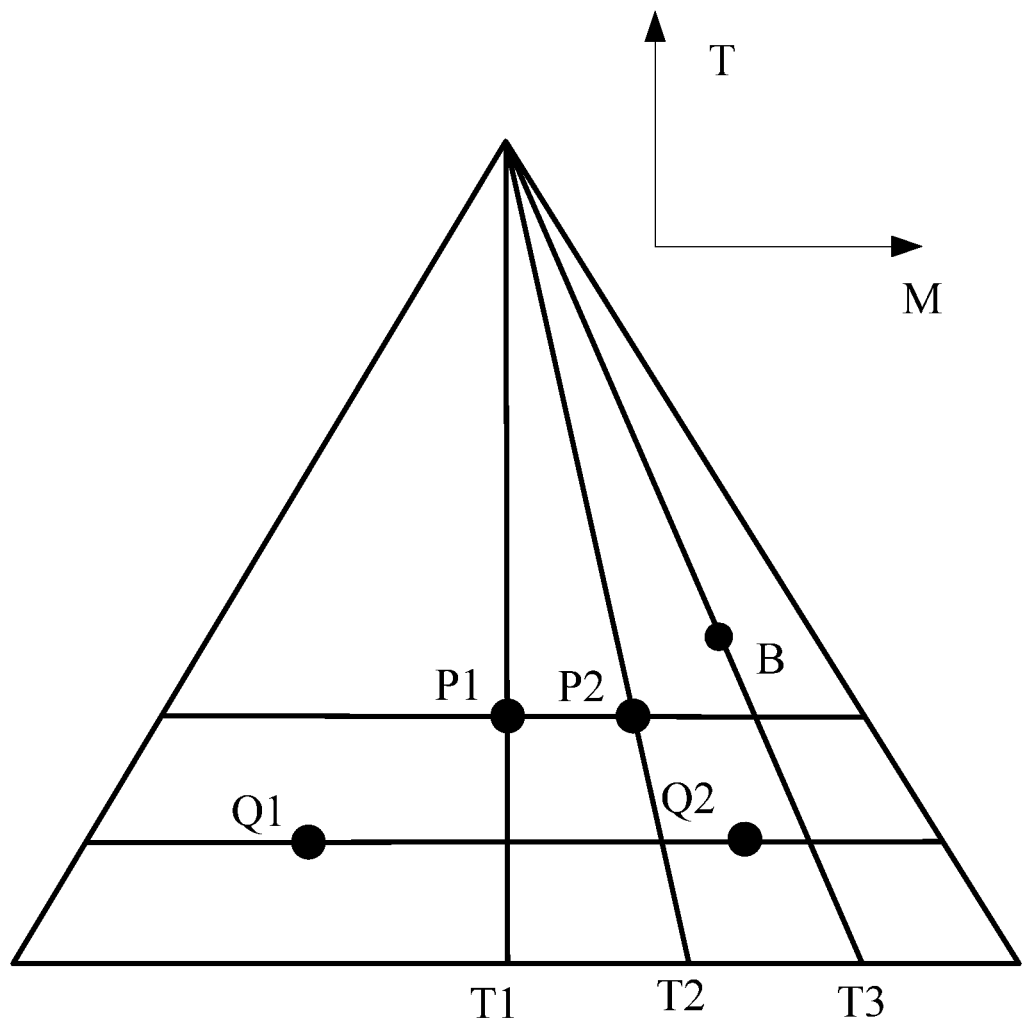
FIG. 10 is a diagram showing an algorithm model for assisting in locating a target spot according to an exemplary embodiment.

Further, as shown in FIG. 10, it is assumed that the first preset mark points P include mark points P1 and P2, the second preset mark points Q include mark points Q1 and Q2, and point B is the target spot, and it is assumed that the coordinate system MON is established on a plane perpendicular to a central ray T of the shooting device; then, in the M-axis direction in the MOT plane, calibrated image position information T1 and T2 of P1 and P2 can be obtained; at this time, the resolution of the projection image can be determined according to the physical distance |P1P2| between the mark points P1 and P2 in the locating coordinate system and the number of pixels between the mark points P1 and P2 in the image coordinate system; further, according to the resolution of the projection image, and the number of pixels between the projection point T1 of the mark point T1 and the projection point T3 of the target spot, the distance $|P1B|_M$ between the mark point P1 and the target spot B in the locating coordinate system can be known; similarly, $|P1B|_N$, $|Q1B|_M$ and $|Q1B|_N$ can be obtained.

Therefore, when the mark point P1 moves by a distance of $|P1B|_M$ along the M-axis and moves by a distance of $|P1B|_N$ along the N-axis, the P1 point coincides with the position of the target spot in the image coordinate system; and when the mark point Q1 moves by a distance of $|Q1B|_M$ along the M-axis and moves by a distance of $|Q1B|_N$ along the N-axis, the Q1 point coincides with the position of the target spot in the image coordinate system. In other words, P1, Q1 and B are on the same projection beam at this time. Therefore, the beam emitting device can be adjusted according to the locating position information of the beam emitting device in the locating coordinate system and the positional relationship between the beam emitting device and points P1 and Q1. The light emitted from the beam emitting device passes through points P1 and Q1, and therefore will necessarily point to the target spot B.

When step 309 and step 310 are respectively executed for a plurality of position points on the virtual path, a planned path formed by the points when the light beam passes through the body surface can be obtained, so that the planned path can assist the medical staff in surgery and improve the accuracy.

Third Embodiment

Figure 11:
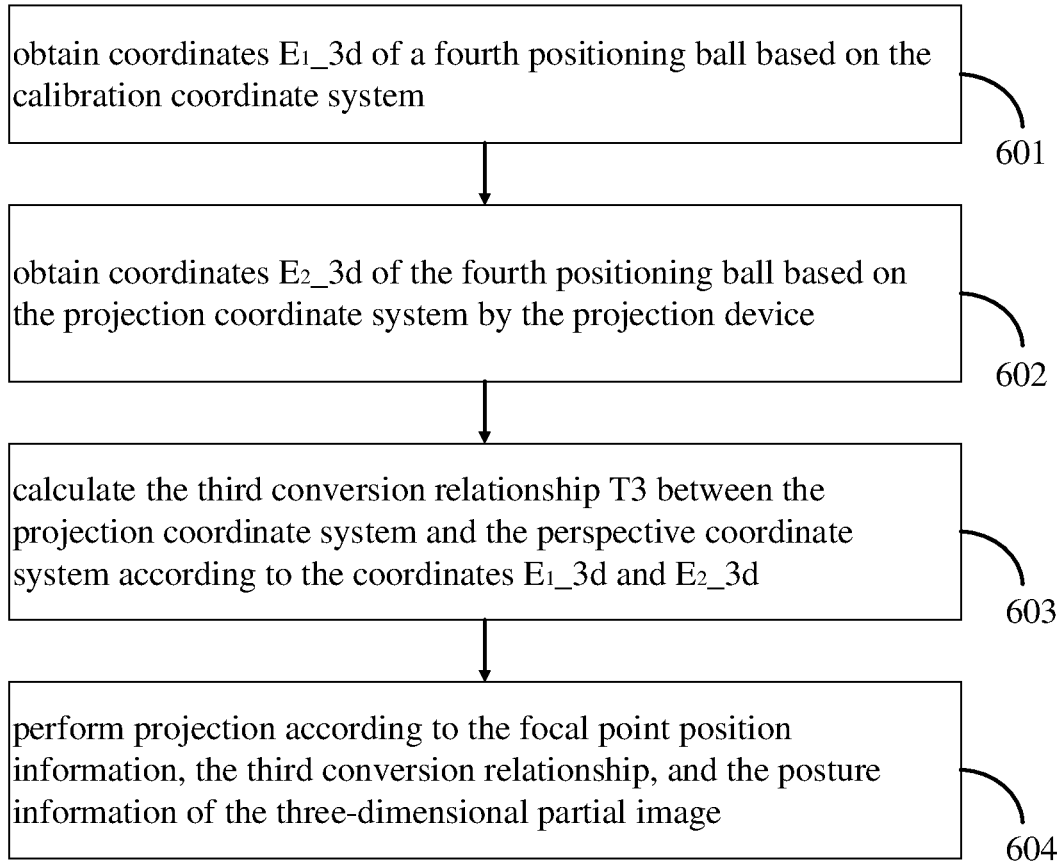
FIG. 11 is a flowchart of yet another projection method according to an exemplary embodiment.

FIG. 11 is a flowchart showing a projection method according to an exemplary embodiment. It can be applied to the device shown in FIG. 4. The system for determining the target spot path may include a projection device 5, and a projection coordinate system can be established based on the projection device. As shown in FIG. 11, the following steps may be included:

In step 601, coordinates $E_1\_3d$ of a fourth locating ball E based on the calibration coordinate system are obtained.

In this embodiment, the fourth locating ball E may be arranged on the calibration device, so that the coordinates $E_1\_3d$ of the fourth locating ball E relative to the calibration coordinate system are known.

In step 602, coordinates $E_2\_3d$ of the fourth locating ball based on the projection coordinate system is obtained by the projection device.

In step 603, the third conversion relationship T3 between the projection coordinate system and the perspective coordinate system is calculated according to the coordinates $E_1\_3d$ and $E_2\_3d$.

In this embodiment, in the above embodiment, since the focal point position information $J\_3d$ of the shooting device is solved by the calibration device, that is, the focal point position information $J\_3d$ is based on the position coordinate information in the calibration coordinate system, and the perspective coordinate system is a coordinate system established by taking the focal point of the shooting device as an origin, the conversion relationship between the calibration coordinate system and the perspective coordinate system is known, which is recorded as a fourth conversion relationship T4.

Therefore, a functional relationship can be established:

$$E_2\_3d=F3(T3,T4,E_1\_3d)$$

Thus, the third conversion relationship T3 is calculated.

In step 604, projection is performed according to the focal point position information, the third conversion relationship, and the posture information of the three-dimensional partial image.

In this embodiment, when the simulated two-dimensional image is matched with the two-dimensional projection, the posture information of the three-dimensional partial image is the posture information $K_1\_3d$ of the actual affected part in the perspective coordinate system and the position information $K_2\_3d=F4$ (T3, $K_1\_3d$) of the affected part in the projection coordinate system; based on this, the projection device can perform projection according to $K_2\_3d$.

The above embodiment includes obtaining the third conversion relationship between the projection coordinate system based on the projection device and the perspective coordinate system based on the shooting device. Further, when the simulated two-dimensional image obtained based on the projection of the three-dimensional partial image is matched with the two-dimensional projection image obtained based on the affected part, the three-dimensional posture information of the three-dimensional partial image is obtained; according to the three-dimensional posture information of the three-dimensional partial image and the virtual path, and the third conversion relationship, the image position information of the affected part in the projection coordinate system is determined, so as to perform projection according to the image position information. When the pointing structure includes the instrument guide channel, the perspective position information of the instrument guide channel in the perspective coordinate system can be obtained according to the second conversion relationship and the locating position information of the instrument guide channel in the locating coordinate system; according to the third conversion relationship and the perspective position information of the instrument guide channel in the perspective coordinate system, the projection position information of the instrument guide channel in the projection coordinate system is obtained, so that projection is performed according to the projection position information; therefore, the surgical operation (i.e., the surgical process) is projected, so that the affected part and the instrument guide channel can be projected to a position that is convenient for the medical staff to view, which makes it convenient to perform the surgical operation.

It can be seen from the above embodiments that in the present application, the three-dimensional posture parameters of the three-dimensional partial image is obtained when the simulated two-dimensional image is matched with the two-dimensional image, so that the perspective position information of the affected part based on the shooting device is obtained; further, by using the coordinate conversion relationship to convert the perspective position information to the projection coordinate system for projection, the medical staff can project the affected part to any suitable position according to needs, which is advantageous for observing the operation process at any time and realizing non-invasive real-time projection. In particular, the projection on the virtual path can provide assistance to the medical staff in insertion of the needle, which is helpful for improving the accuracy of the operation.

Fourth Embodiment

Figure 13:
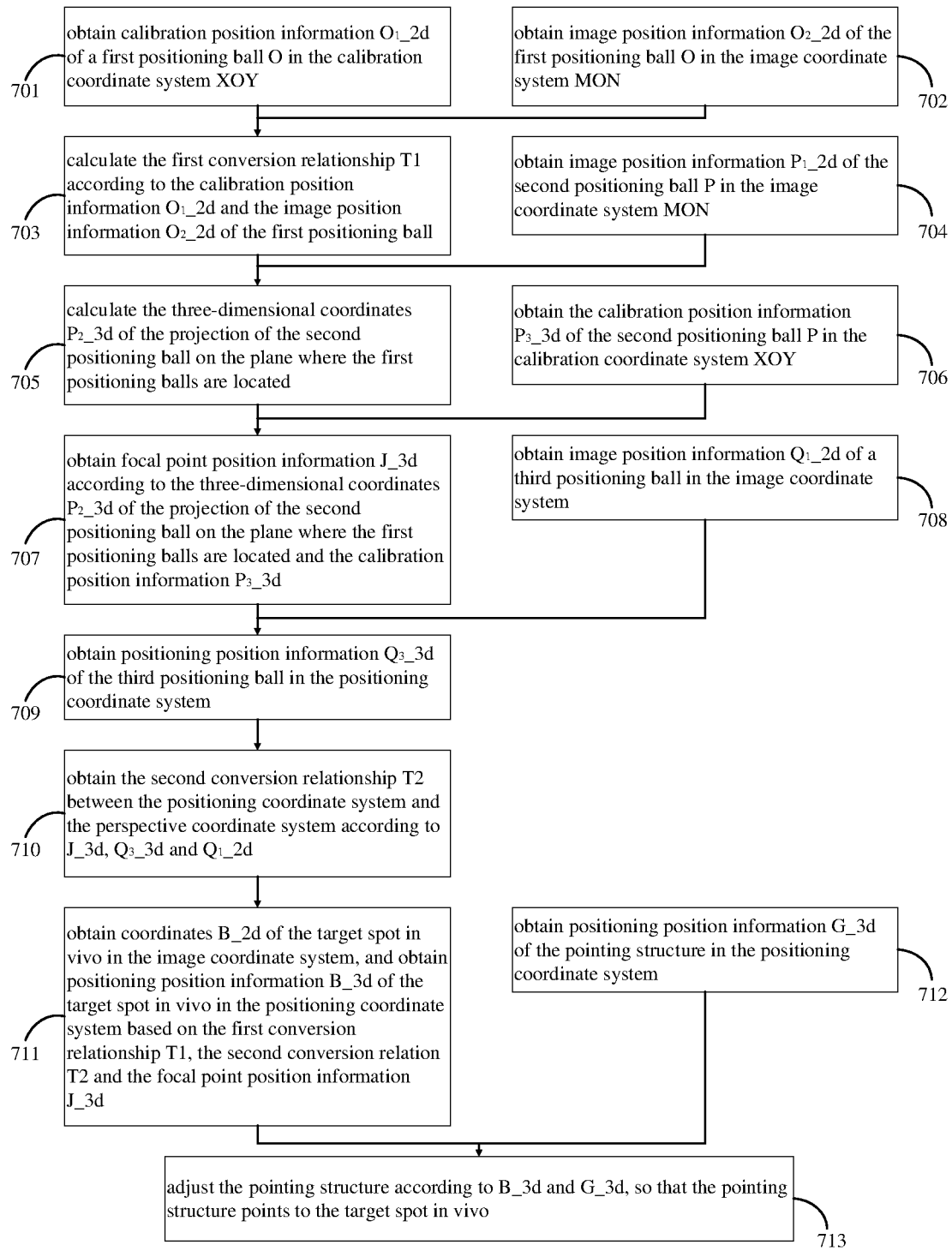
FIG. 13 is a flowchart of a method for locating a target spot according to an exemplary embodiment.

FIG. 13 is a flowchart of another method for locating a target spot according to an exemplary embodiment. As shown in FIG. 13, the method for locating a target spot may include the following steps.

In step 701, calibration position information $O_1\_2d$ of a first locating ball (that is, a first preset mark point) 0 in the calibration coordinate system XOY is obtained. For details, reference may be made to step 301.

In step 702, image position information $O_2\_2d$ of the first locating ball O in the image coordinate system MON is obtained. For details, reference may be made to step 302.

In step 703, according to the calibration position information $O_1\_2d$ of the first locating ball 211 and the image position information $O_2\_2d$ of the first locating ball 211, the first conversion relationship T1 between the calibration coordinate system and the image coordinate system is calculated. For details, reference may be made to steps 303 to 304.

In step 704, image position information $P_1\_2d$ of the second locating ball 221 in the image coordinate system MON is obtained.

In this embodiment, based on the projection image of the calibration device 2 under the shooting device 1, and further based on the image coordinate system MON, the image position information of each of the second locating balls 221 can be obtained, and the image position information $P_1\_2d$ of the second locating balls 221 may include P1 (M1, N1), P2 (M2, N2) . . . Pn (Mn, Nn).

In step 705, according to the first conversion relationship T1 and the image position information of the second locating balls 221, the three-dimensional coordinates $P_2\_3d$ of the projection of the second locating ball on the plane where the first locating balls are located are calculated.

In this embodiment, the plane where the first locating balls 211 are located is the position of the calibration plate 21. Through the first conversion relationship T1, projection coordinates $P_3\_2d$ of the second locating balls 221 on the calibration plate 21 can be obtained. The $P_3\_2d$ may include P1 (X1, Y1), P2 (X2, Y2) . . . Pn (Xn, Yn), and in this embodiment, it can be assumed that the calibration coordinate system is located on the calibration plate, so the Z coordinate of the projection point of the second locating ball 221 on the calibration plate 21 is zero, thereby obtaining the three-dimensional coordinates $P_2\_3d$ projected by the second locating ball 221: P1 (X1, Y1, 0), P2 (X2, Y2, 0) . . . Pn (Xn, Yn, 0).

In step 706, the calibration position information $P_3\_3d$ of the second locating ball P in the calibration coordinate system XOY is obtained.

In this embodiment, according to the relative position relationship between the calibration plate 21 and the first identification plate 22, the calibration position information of each second locating ball on the first identification plate 22 in the calibration coordinate system can be obtained, and the calibration position information $P_3\_3d$ may include Pj1 (X1, Y1, Z1), Pj2 (X2, Y3, Z3) . . . Pj3 (X1, Y1, Z1).

In step 707, focal point position information $J\_3d$ is obtained according to $P_2\_3d$ and $P_3\_3d$.

In this embodiment, each second locating ball 221 on the first identification plate 22 may form a projection point on the calibration plate 21. In other words, the projection of the second locating ball 221 on the calibration plate 21 each has a corresponding second locating ball 221 in a physical space. For example, assuming that the calibration position information of a second locating ball 221 in the calibration coordinate system is Pj1 (X1, Y1, Z1), and the position information of the projection of the second locating ball 221 on the calibration plate 21 is P1 (X1, Y1, 0), then a straight line connecting the two points P1 (X1, Y1, 0) and Pj1 (X1, Y1, Z1) will necessarily pass through the light source. Therefore, through the plurality of second locating balls 221, a plurality of straight lines passing through the light source can be obtained, and thus the position information of the light source, that is, the focal point position information $J\_3d$, can be calculated. The Z-axis coordinate of the focal point position information $J\_3d$ is the distance between the light source and the projection imaging plane. Based on the focal point position information $J\_3d$, a projection transformation matrix A between the three-dimensional coordinates of any point in the perspective coordinate system and the corresponding point in the projection image can be obtained.

In step 708, image position information $Q_1\_2d$ of a third locating ball in the image coordinate system is obtained.

In this embodiment, since there are a plurality of third locating balls 311, based on the image coordinate system MON, the two-dimensional coordinates $Q_1\_2d$ may include Q1 (M1, N1), Q2 (M2, N2) . . . Qn (Mn, Nn)).

In step 709, locating position information $Q_3\_3d$ of the third locating ball 311 in the locating coordinate system is obtained.

In this embodiment, the locating coordinate system can be established on the locating device 3, and since the relative position relationships between the various structures on the locating device 3 are known, the locating position information $Q_3\_3d$ of the third locating balls 311 in the locating coordinate system can be obtained.

In step 710, according to the focal point coordinate information $J\_3d$, the locating position information $Q_3\_3d$ of the third locating balls 311, and the two-dimensional coordinates $Q_1\_2d$ of the third locating balls in the image coordinate system, the second conversion relationship T2 between the perspective coordinate system and the locating coordinate system is obtained.

In this embodiment, it can be assumed that the perspective position information of the third locating balls in the perspective coordinate system is $Q_2\_3d$, then $Q_2\_3d=F1$ (T2, $Q_3\_3d$) can be obtained, and the projection transformation matrix A of the shooting device can be obtained according to the focal point coordinate information $J\_3d$, that is, the following functional relationship can be obtained: the third locating ball Q's image position information $Q_1\_2d=F2$ (T1, A, $Q_2\_3d$). Therefore, in combination with $Q_1\_2d=F2$ (T1, A, $Q_2\_3d$) and $Q_2\_3d=F1$ (T2, $Q_3\_3d$), the third locating ball Q's image position information $Q_1\_2d=F3$ (T1, A, T2, $Q_3\_3d$) can be obtained. Since the image position information $Q_1\_2d$ of the third locating balls Q, the first conversion relationship T1, the projection transformation matrix A, and the locating position information $Q_3\_3d$ of the third locating balls 311 are all known, the second conversion relationship T2 between the locating coordinate system and the perspective coordinate system can be calculated. For example, the matrix can be continuously matched through the optimization algorithm, and the optimal matrix obtained is the second conversion relationship. For example, the least square method or other optimization algorithms may be used, to which the present application does not impose any limitation.

In step 711, image coordinate information $B\_2d$ of the target spot in vivo (that is, image information of the surgical path on the two-dimensional projection image) in the image coordinate system is obtained, and locating position information $B\_3d$ of the target spot in vivo in the locating coordinate system is obtained based on the first conversion relationship T1, the focal point position information $J\_3d$ and the second conversion relation T2.

In this embodiment, the following functional relationship can be established:

$$B\_2d=F4(T1,T2,A,B\_3d)$$

Based on this, the three-dimensional coordinates $B\_3d$ of the target spot in vivo based on the locating device 3 can be obtained.

In step 712, locating position information $G\_3d$ of the pointing structure 32 in the locating coordinate system is obtained.

In this embodiment, since the relative position relationship between the pointing structure 32 and the second identification plate 31 is fixed, the locating position information of the pointing structure 32 can be calculated from the position information of the second identification plate 31. Of course, the locating position information $G\_3d$ of the pointing structure 32 may also be obtained in other ways, such as in a pre-stored way, to which the present application does not impose any limitation.

In step 713, according to the locating position information $B\_3d$ of the target spot in vivo in the locating coordinate system and the locating position information $G\_3d$ of the pointing structure 32, the pointing structure 32 is adjusted so that the pointing structure 32 points to the target spot in vivo.

In this embodiment, since the locating position information of the target spot in vivo and the pointing structure 32 in the locating coordinate system each is known, the position of the beam emitting structure 32 can be adjusted by the movement of the mechanical arm 34 or a joint movement of the mechanical arm 34 and the sliding base 35.

In the foregoing embodiment, after step 710, the following steps may also be executed to realize the three-dimensional locating of the mechanical arm:

obtaining a three-dimensional partial image and a virtual path pointing to the virtual target spot;

projecting the affected part to obtain a two-dimensional projection image, in which a calibrated two-dimensional projection image is obtained through the first conversion relationship T1;

projecting the three-dimensional partial image to obtain a simulated two-dimensional image;

obtaining a degree of coincidence between the simulated two-dimensional image and the calibrated two-dimensional projection image, and when the degree of coincidence is not smaller than a preset threshold, determining that the simulated two-dimensional image is matched with the two-dimensional projection image;

obtaining posture information of the virtual path, and obtaining locating position information of the virtual path in the locating coordinate system according to the posture information of the virtual path and the second conversion relationship;

obtaining the locating position information $G\_3d$ of the beam emitting component in the locating coordinate system; and adjusting the beam emitting component according to the locating position information of the beam emitting component and the virtual path in the locating coordinate system, so that the light emitted from the beam emitting component is matched with the virtual path.

In this embodiment, since the locating position information of the beam emitting component and the surgical path to be established in the locating coordinate system each is known, an adjustment instruction can be generated to adjust the beam emitting component.

After considering the specification and practicing the contents disclosed herein, those skilled in the art will easily think of other embodiments of the present application. The present application is intended to cover any variations, uses, or adaptive changes of the present application. These variations, uses, or adaptive changes follow the general principles of the present application and include common knowledge or customary technical means in the art that are not disclosed in the present application. The specification and the embodiments are only regarded as exemplary, and the true scope and spirit of the present application are defined by the appended claims.

It should be understood that the present application is not limited to the precise structures described above and shown in the drawings, and various modifications and changes may be made without departing from the scope thereof. The scope of the present application is only limited by the appended claims.

The invention claimed is:

1. A method for determining a target spot path, which is applied to a determining system comprising a shooting device and a locating device that are separate from each other, and a calibration device connected to the shooting device, the locating device comprising a pointing structure, and the method for determining the target spot path comprising:
   S1: obtaining a three-dimensional partial image for an affected part and a virtual path located in the three-dimensional partial image;
   S2: matching a simulated two-dimensional image obtained based on projection of the three-dimensional partial image with a two-dimensional projection image obtained based on the affected part;
   S3: determining a surgical guide path on the two-dimensional projection image that corresponds to the virtual path according to position information of the virtual path on the simulated two-dimensional image, when the simulated two-dimensional image and the two-dimensional projection image are matched;
   S4: obtaining three-dimensional posture information of the virtual path on the three-dimensional partial image as perspective coordinate information of the surgical guide path based on a perspective coordinate system, when the simulated two-dimensional image and the two-dimensional projection image are matched, wherein the perspective coordinate system is formed based on the shooting device;
   adjusting the pointing structure according to the perspective coordinate information of the surgical guide path, and a second conversion relationship between the perspective coordinate system and a locating coordinate system based on the locating device, so that a pointing direction of the pointing structure is matched with the surgical guide path corresponding to the virtual path, wherein the calibration device comprises a calibration plate and a first identification plate, the calibration plate is provided with a plurality of first preset mark points, and the first identification plate is provided with a plurality of second preset mark points; in a projection direction, the calibration plate and the first identification plate are arranged in parallel with each other at an interval;
   wherein in S3, the method further comprises:
   S31: obtaining first image position information of a plurality of position points on the two-dimensional projection image that correspond to the virtual path; and
   S32: adjusting the pointing structure based on the first image position information, so that the pointing direction of the pointing structure sequentially points to a plurality of target spots at the affected part that correspond to a plurality of position points on the surgical guide path
   wherein in S32, the step of adjusting the pointing structure based on the first image position information comprises:
   obtaining image position information of a projection path on the two-dimensional projection image that is matched with the virtual path, according to image position information of the virtual path on the simulated two-dimensional image;
   adjusting the pointing structure according to image position information of a plurality of position points on the projection path;
   wherein the calibration device comprises a calibration plate and a first identification plate, the calibration plate is provided with a plurality of first preset mark points, and the first identification plate is provided with a plurality of second preset mark points; in a projection direction, the calibration plate and the first identification plate are arranged in parallel with each other at an interval;
   in step S32, the step of adjusting the pointing structure based on the first image position information comprises:
   obtaining calibration position information of each of the first preset mark points on a first plane and each of the second preset mark points on a second plane in a calibration coordinate system;
   obtaining image position information of each of the first preset mark points on the first plane and each of the second preset mark points on the second plane in an image coordinate system, wherein the image coordinate system is formed based on a projection image of the calibration device; and
   adjusting the pointing structure according to the calibration position information and the image position information of the first preset mark points, the calibration position information and the image position information of the second preset mark points, and the first image position information of any position point on the virtual path.

2. The method for determining the target spot path according to claim 1, wherein in S2, the step of matching the simulated two-dimensional image obtained based on the projection of the three-dimensional partial image with the two-dimensional projection image obtained based on the affected part comprises:
   S21: performing a perspective projection on the affected part to obtain the two-dimensional projection image;
   S22: projecting the three-dimensional partial image to obtain the simulated two-dimensional image; and
   S23: obtaining a degree of coincidence of the simulated two-dimensional image and the two-dimensional projection image, and determining that the simulated two-dimensional image is matched with the two-dimensional projection image when the degree of coincidence is not smaller than a preset threshold.

3. The method for determining the target spot path according to claim 2, wherein in step S23, the step of obtaining the degree of coincidence of the simulated two-dimensional image and the two-dimensional projection image comprises:
   extracting a first projection area in the simulated two-dimensional image and a second projection area in the two-dimensional projection image; and
   calculating the degree of coincidence according to a degree of edge contour matching between the first projection area and the second projection area.

4. The method for determining the target spot path according to claim 2, wherein in S23, the step of obtaining the degree of coincidence of the simulated two-dimensional image and the two-dimensional projection image comprises:
   segmenting both the simulated two-dimensional image and the two-dimensional projection image in a preset direction according to a preset ratio; and matching each segmented area of the simulated two-dimensional image with a corresponding segmented area of the two-dimensional projection image to obtain the degree of coincidence.

5. The method for determining the target spot path according to claim 2, wherein in S23, if the degree of coincidence is smaller than the preset threshold, a spatial posture of the three-dimensional partial image is adjusted; and projection parameters for the three-dimensional partial image are adjusted.

6. The method for determining the target spot path according to claim 5, wherein the step of adjusting the spatial posture of the three-dimensional partial image comprises at least one of the following:
adjusting a rotational angle of the three-dimensional partial image with respect to at least one coordinate axis; and
adjusting a displacement of the three-dimensional partial image with respect to at least one coordinate axis; and
the step of adjusting the projection parameters for the three-dimensional partial image comprises at least one of the following:
adjusting a focal length;
adjusting a position of a virtual light source; and
adjusting an imaging resolution, wherein the imaging resolution is related to a size of a projection imaging plane of the three-dimensional partial image and an image size of the simulated two-dimensional image.

7. The method for determining the target spot path according to claim 1, further comprising:
determining a first conversion relationship between the calibration coordinate system and the image coordinate system according to the calibration position information of the plurality of first preset mark points on the calibration device in the calibration coordinate system and the image coordinate information of the plurality of first preset mark points on the calibration device in the image coordinate system; and
obtaining the calibrated two-dimensional projection image according to the first conversion relationship.

8. The method for determining the target spot path according to claim 7, wherein the locating device comprises a second identification plate which is provided with a plurality of third preset mark points, and the calibration device is separate from the locating device; and
the second conversion relationship is obtained in the following manner:
obtaining the first conversion relationship between the calibration coordinate system and the image coordinate system and focal point position information of the shooting device; and
determining the second conversion relationship according to the focal point position information of the shooting device, locating coordinate information of the second identification plate in the locating coordinate system, the first conversion relationship and image coordinate information of the second identification plate in the image coordinate system, wherein the perspective coordinate system is related to the focal point position information.

9. The method for determining the target spot path according to claim 8, wherein the focal point position information of the shooting device is determined based on the image position information of the plurality of second preset mark points in the image coordinate system, the calibration position information in the calibration coordinate system, and the first conversion relationship.

10. The method for determining the target spot path according to claim 9, wherein in S4, the step of adjusting the pointing structure so that the pointing direction of the pointing structure is matched with the surgical guide path corresponding to the virtual path comprises:
obtaining locating position information of the surgical guide path in the locating coordinate system according to perspective coordinate information of the target spot path and the second conversion relationship; and
adjusting the pointing structure according to the locating position information of the surgical guide path and locating position information of the pointing structure in the locating coordinate system, so that the pointing direction of the pointing structure coincides with an extending direction of the surgical guide path.

11. The method for determining the target spot path according to claim 10, wherein the pointing structure comprises a beam emitting component;
in S3, a light beam emitted from the beam emitting component points to the target spot; and
in S4, the light beam emitted from the beam emitting component is matched with the target spot path;
alternatively, the pointing structure comprises an instrument guide channel;
in step S3, a central axis of the instrument guide channel points to the target spot; and
in step S4, the central axis of the instrument guide channel is matched with the target spot path.

12. The method for determining the target spot path according to claim 1, wherein the system for determining the target spot path further comprises a projection device, and in S4, the method further comprises:
obtaining a third conversion relationship between a projection coordinate system based on the projection device and the perspective coordinate system; and
determining projection position information of the affected part in the projection coordinate system according to the three-dimensional partial image, the three-dimensional posture information of the virtual path, and the third conversion relationship, so as to perform projection according to the projection position information.

13. The method for determining the target spot path according to claim 12, wherein the step of obtaining the third conversion relationship between the projection coordinate system based on the projection device and the perspective coordinate system comprises:
obtaining, by the projection device, projection position information of the preset mark points in the calibration device in the projection coordinate system; and
determining the third conversion relationship between the projection coordinate system and the perspective coordinate system according to the projection position information of the third preset mark points and coordinate information of the third preset mark points in the perspective coordinate system.

14. The method for determining the target spot path according to claim 13, wherein if the pointing structure comprises an instrument guide channel, the method further comprises:
obtaining position information of the instrument guide channel in the perspective coordinate system, and obtaining projection position information of the instrument guide channel in the projection coordinate system according to the third conversion relationship, so as to perform projection according to the projection position information of the instrument guide channel.

15. The method for determining the target spot path according to claim 13, wherein the pointing structure is adjusted according to locating position information of the pointing structure in the locating coordinate system, the focal point position information, the first conversion relationship, the second conversion relationship, and position information of projected target spots in the image coordinate system, so that the pointing direction of the pointing structure points to the target spots in vivo.

16. The method for determining the target spot path according to claim 14, wherein the pointing structure is adjusted according to locating position information of the pointing structure in the locating coordinate system, the focal point position information, the first conversion relationship, the second conversion relationship, and position information of projected target spots in the image coordinate system, so that the pointing direction of the pointing structure points to the target spots in vivo.

17. The method for determining the target spot path according to claim 4, wherein in S23, if the degree of coincidence is smaller than the preset threshold, a spatial posture of the three-dimensional partial image is adjusted; and projection parameters for the three-dimensional partial image are adjusted.

* * * * *